US012178786B2

(12) United States Patent
Li et al.

(10) Patent No.: US 12,178,786 B2
(45) Date of Patent: Dec. 31, 2024

(54) COMBINATION OF CELLULAR IMMUNOTHERAPY

(71) Applicant: CRAGE medical Co., Limited, Kowloon (HK)

(72) Inventors: Zonghai Li, Shanghai (CN); Xiuqi Wu, Shanghai (CN)

(73) Assignee: CRAGE medical Co., Limited, Mongkok Kowloon (HK)

(*) Notice: Subject to any disclaimer, the term of this patent is extended or adjusted under 35 U.S.C. 154(b) by 1108 days.

(21) Appl. No.: 16/966,789

(22) PCT Filed: Feb. 2, 2019

(86) PCT No.: PCT/CN2019/074535
§ 371 (c)(1),
(2) Date: Oct. 2, 2020

(87) PCT Pub. No.: WO2019/149279
PCT Pub. Date: Aug. 8, 2019

(65) Prior Publication Data
US 2021/0113614 A1   Apr. 22, 2021

(30) Foreign Application Priority Data

Feb. 2, 2018   (CN) .......................... 201810107786.5
Feb. 8, 2018   (CN) .......................... 201810129611.4
Jan. 4, 2019   (CN) .......................... 201910008444.2

(51) Int. Cl.
*A61P 35/00* (2006.01)
*A61K 31/4402* (2006.01)
*A61K 38/17* (2006.01)
*A61K 39/00* (2006.01)
*C07K 16/28* (2006.01)

(52) U.S. Cl.
CPC ...... *A61K 31/4402* (2013.01); *A61K 38/1774* (2013.01); *A61K 39/4611* (2023.05); *A61K 39/4631* (2023.05); *A61K 39/464474* (2023.05); *A61P 35/00* (2018.01); *C07K 16/2815* (2013.01); *C07K 16/2818* (2013.01); *A61K 2239/31* (2023.05); *A61K 2239/38* (2023.05); *A61K 2239/53* (2023.05)

(58) Field of Classification Search
CPC ................ A61K 35/17; A61K 31/4402; A61K 38/1774; A61K 39/001174; A61K 2039/5156; A61K 2039/5158; A61K 2039/844; A61K 39/39558; A61K 31/44; A61K 31/4412; A61K 39/0011; A61K 2300/00; A61P 35/00; C07K 16/2815; C07K 16/2818; C07K 16/303; C07K 2319/03; C07K 14/7051
See application file for complete search history.

(56) References Cited

U.S. PATENT DOCUMENTS

2019/0046659 A1* 2/2019 Wang .................. A61K 39/395

FOREIGN PATENT DOCUMENTS

| CN | 102325548 A | 1/2012 |
| CN | 105457021 A | 4/2016 |
| CN | 106471004 A | 3/2017 |
| JP | 2013511549 A | 4/2013 |
| JP | 2017507955 A | 3/2017 |
| JP | 2017527289 A | 9/2017 |
| JP | 2018500337 A | 1/2018 |
| JP | 2018501192 A | 1/2018 |
| WO | 2017020812 A1 | 2/2017 |
| WO | 2017151044 A1 | 9/2017 |
| WO | 2017186121 A1 | 11/2017 |
| WO | 2019024933 A1 | 2/2019 |
| WO | 2019/149279 A1 | 8/2019 |
| WO | 2019210863 A1 | 11/2019 |

OTHER PUBLICATIONS

Trinh T et al. GPC3-specific chimeric antigen receptor T cell in combination with Sorafenib as a novel therapeutic treatment for hepatocellular carcinoma. Cancer Res (2016) 76 (14_Supplement): 2316 (Year: 2016).*
Sigma-Aldrich Sorafenib (https://www.sigmaaldrich.com/US/en/product/sigma/sml2653 accessed Jan. 2024) (Year: 2024).*
Jiang Z et al. Anti-GPC3-CAR T Cells Suppress the Growth of Tumor Cells in Patient-Derived Xenografts of Hepatocellular Carcinoma (Front. Immunol. 2017 7:690. doi: 10.3389/fimmu.2016. 00690 1-10) (Year: 2017).*
The Jackson Laboratory NOD.Cg-Prkdcscid Il2rgtm1Wjl/SzJ weight (https://www.jax.org/jax-mice-and-services/strain-data-sheet-pages/body-weight-chart-005557) (Year: 2024).*
Bayer et al. Nexvar prescribing information 2010 (https://www.accessdata.fda.gov/drugsatfda_docs/label/2010/021923s008s009lbl.pdf) (Year: 2010).*
Department of Health and Human Services FDA. (Federal Register 2006 71 (15) 3922-3997) (Year: 2006).*
NCI et al. Regorafenib Becomes First FDA-Approved Drug for Liver Cancer in Nearly a Decade (https://www.cancer.gov/news-events/cancer-currents-blog/2017/fda-regorafenib-liver, May 24, 2017) (Year: 2017).*
International Preliminary Report on Patentability, PCT/CN2019/074535, dated Aug. 4, 2020, 11 pages.

(Continued)

*Primary Examiner* — Karen A. Canella
*Assistant Examiner* — John J Skoko, III
(74) *Attorney, Agent, or Firm* — Nelson Mullins Riley & Scarborough LLP; Jill Gorny Sloper, Esq.

(57) ABSTRACT

Provided in the present invention is a method for treating tumor. An immune effector cell and a second treatment agent are applied to individual suffering from tumor, wherein the immune effector cell expresses a receptor for recognizing tumor antigen, and wherein the second treatment agent is a compound of formula I or a pharmaceutically acceptable salt thereof.

16 Claims, 11 Drawing Sheets

Specification includes a Sequence Listing.

(56) References Cited

OTHER PUBLICATIONS

International Search Report and Written Opinion, PCT/CN2019/074535, dated May 6, 2019, 20 pages.
Extended European search Report, European U.S. Appl. No. 19/748,023, dated Nov. 18, 2021, 87 pages.
Hui-Yen C. et al., "Serial low doses of sorafenib enhance therapeutic efficacy of adoptive T cell therapy in a murine model by improving tumor microenvironment," PLOS ONE, vol. 9 (10):1-11 (2014).
Trinh, T. et al., "GPC3-specific chimeric antigen receptor T cell in combination with Sorafenib as a novel therapeutic treatment for hepatocellular carcinoma," Immunology, Abstract 2316:2316-2316 (2016).
Zhang, Q. et al., "Combination Therapy with EpCAM-CAR-NK-92 Cells and Regorafenib against Human Colorectal Cancer Models," Journal Of Immunolgy Research, vol. 2018: 12 pages (2018).

* cited by examiner

```
                        SEQUENCE LISTING

<160> NUMBER OF SEQ ID NOS: 24

<210> SEQ ID NO 1
<211> LENGTH: 216
<212> TYPE: DNA
<213> ORGANISM: Artificial sequence
<220> FEATURE:
<223> OTHER INFORMATION: Artificially synthesized sequence

<400> SEQUENCE: 1
actactacca agccagtgct gcgaactccc tcacctgtgc accctaccgg gacatctcag    60
ccccagagac cagaagattg tcggccccgt ggctcagtga aggggaccgg attggacttc   120
gcctgtgata tttacatctg gcacccttg gccggaatct gcgtggccct tctgctgtcc    180
ttgatcatca ctctcatctg ctaccacagg agccga                             216

<210> SEQ ID NO 2
<211> LENGTH: 123
<212> TYPE: DNA
<213> ORGANISM: Artificial sequence
<220> FEATURE:
<223> OTHER INFORMATION: Artificially synthesized sequence

<400> SEQUENCE: 2
aatagtagaa ggaacagact ccttcaaagt gactacatga acatgactcc ccggaggcct    60
gggctcactc gaaagcctta ccagccctac gcccctgcca gagactttgc agcgtaccgc   120
ccc                                                                 123

<210> SEQ ID NO 3
<211> LENGTH: 321
<212> TYPE: DNA
<213> ORGANISM: Artificial sequence
<220> FEATURE:
<223> OTHER INFORMATION: Artificially synthesized sequence
```

```
<400> SEQUENCE: 3
agcaggagtg cagagactgc tgccaacctg caggacccca accagctcta caatgagctc    60
aatctagggc gaagagagga atatgacgtc ttggagaaga agcgggctcg ggatccagag   120
atgggaggca acagcagag gaggaggaac ccccaggaag gcgtatacaa tgcactgcag   180
aaagacaaga tggcagaagc ctacagtgag atcggcacaa aaggcgagag cggagaggc   240 aaggggcacg atggccttta ccagggtctc agcactgcca ccaaggacac ctatgatgcc   300
ctgcatatgc agaccctggc c                                            321

<210> SEQ ID NO 4
<211> LENGTH: 81
<212> TYPE: DNA
<213> ORGANISM: Artificial sequence
<220> FEATURE:
<223> OTHER INFORMATION: Artificially synthesized sequence

<400> SEQUENCE: 4
atggcctcac cgttgacccg ctttctgtcg ctgaacctgc tgctgctggg tgagtcgatt    60
atcctgggga gtggagaagc t                                             81

<210> SEQ ID NO 5
<211> LENGTH: 729
<212> TYPE: DNA
<213> ORGANISM: Artificial sequence
<220> FEATURE:
<223> OTHER INFORMATION: Artificially synthesized sequence

<400> SEQUENCE: 5
gaggtgcagc tggtgcagag cggcgccgag gtgaagaagc ccggcgccag cgtgaaggtg    60
agctgcaagg ccagcggcta caccttcagc gactacgaga tgcactgggt gcggcaggcc   120
cccggccagg gcctggagtg gatgggcgcc atccaccccg gcagcggcga caccgcctac   180
aaccagcggt tcaagggccg ggtgaccatc accgccgaca gagcaccag caccgcctac   240 atggagctga gcagcctgcg gagcgaggac accgccgtgt actactgcgc ccggttctac   300
agctacgcct actgggggcca gggcaccctg gtgaccgtga gcgccggtgg aggcggttca   360
ggcggaggtg gttctggcgg tggcggatcg gacatcgtga tgacccagac cccccctgagc   420 ctgcccgtga cccccggcga gcccgccagc atcagctgcc ggagcagcca gagcctggtg   480
cacagcaacg gcaacaccta cctgcagtgg tacctgcaga gcccggcca gagcccccag   540 ctgctgatct acaaggtgag caaccggttc agcggcgtgc ccgaccggtt cagcggcagc   600
ggcagcggca ccgacttcac cctgaagatc agccgggtgg aggccgagga cgtgggcgtg   660
tactactgca gccagagcat ctacgtgccc tacaccttcg gccagggcac caagctggag   720
atcaaacgt                                                          729

<210> SEQ ID NO 6
<211> LENGTH: 63
<212> TYPE: DNA
<213> ORGANISM: Artificial sequence
<220> FEATURE:
<223> OTHER INFORMATION: Artificially synthesized sequence

<400> SEQUENCE: 6
atggccttac cagtgaccgc cttgctcctg ccgctggcct tgctgctcca cgccgccagg    60
ccg                                                                63
```

<210> SEQ ID NO 7
<211> LENGTH: 135
<212> TYPE: DNA
<213> ORGANISM: Artificial sequence
<220> FEATURE:
<223> OTHER INFORMATION: Artificially synthesized sequence

<400> SEQUENCE: 7

```
accacgacgc cagcgccgcg accaccaaca ccggcgccca ccatcgcgtc gcagcccctg      60
tccctgcgcc cagaggcgtg ccggccagcg gcgggggggcg cagtgcacac gagggggctg    120
gacttcgcct gtgat                                                      135
```

<210> SEQ ID NO 8
<211> LENGTH: 123
<212> TYPE: DNA
<213> ORGANISM: Artificial sequence
<220> FEATURE:
<223> OTHER INFORMATION: Artificially synthesized sequence

<400> SEQUENCE: 8

```
aggagtaaga ggagcaggct cctgcacagt gactacatga acatgactcc ccgccgcccc     60
gggccaaccc gcaagcatta ccagccctat gccccaccac gcgacttcgc agcctatcgc    120
tcc                                                                  123
```

<210> SEQ ID NO 9
<211> LENGTH: 339
<212> TYPE: DNA
<213> ORGANISM: Artificial sequence
<220> FEATURE:
<223> OTHER INFORMATION: Artificially synthesized sequence

<400> SEQUENCE: 9

```
agagtgaagt tcagcaggag cgcagacgcc cccgcgtacc agcagggcca gaaccagctc      60
tataacgagc tcaatctagg acgaagagag gagtacgatg ttttggacaa gagacgtggc    120
cgggaccctg agatggggggg aaagccgcag agaaggaaga accctcagga aggcctgtac    180
aatgaactgc agaaagataa gatggcggag gcctacagtg agattgggat gaaaggcgag    240
cgccggaggg gcaaggggca cgatggcctt taccagggtc tcagtacagc caccaaggac    300
acctacgacg cccttcacat gcaggccctg ccccctcgc                           339
```

<210> SEQ ID NO 10
<211> LENGTH: 81
<212> TYPE: DNA
<213> ORGANISM: Artificial sequence
<220> FEATURE:
<223> OTHER INFORMATION: Artificially synthesized sequence

<400> SEQUENCE: 10

```
ttttgggtgc tggtggtggt tggtggagtc ctggcttgct atagcttgct agtaacagtg      60
gcctttatta ttttctgggt g                                               81
```

<210> SEQ ID NO 11
<211> LENGTH: 579
<212> TYPE: PRT
<213> ORGANISM: Artificial sequence
<220> FEATURE:
<223> OTHER INFORMATION: Artificially synthesized sequence

<400> SEQUENCE: 11

```
Met Ala Gly Thr Val Arg Thr Ala Cys Leu Leu Val Ala Met Leu Leu
1               5                   10                  15
```

```
Gly Leu Gly Cys Leu Gly Gln Ala Gln Pro Pro Pro Asp Ala
            20                  25                  30

Thr Cys His Gln Val Arg Ser Phe Gln Arg Leu Gln Pro Gly Leu
        35                  40                  45

Lys Trp Val Pro Glu Thr Pro Val Pro Gly Ser Asp Leu Gln Val Cys
50                      55                  60

Leu Pro Lys Gly Pro Thr Cys Cys Ser Arg Lys Met Glu Glu Lys Tyr
65                  70                  75                  80

Gln Leu Thr Ala Arg Leu Asn Met Glu Gln Leu Leu Gln Ser Ala Ser
                85                  90                  95

Met Glu Leu Lys Phe Leu Ile Ile Gln Asn Ala Ala Val Phe Gln Glu
            100                 105                 110

Ala Phe Glu Ile Val Val Arg His Ala Lys Asn Tyr Thr Asn Ala Met
            115                 120                 125

Phe Lys Asn Asn Tyr Pro Ser Leu Thr Pro Gln Ala Phe Glu Phe Val
    130                 135                 140

Gly Glu Phe Phe Thr Asp Val Ser Leu Tyr Ile Leu Gly Ser Asp Ile
145                 150                 155                 160

Asn Val Asp Asp Met Val Asn Glu Leu Phe Asp Ser Leu Phe Pro Val
                165                 170                 175

Ile Tyr Thr Gln Met Met Asn Pro Gly Leu Pro Glu Ser Val Leu Asp
            180                 185                 190

Ile Asn Glu Cys Leu Arg Gly Ala Arg Arg Asp Leu Lys Val Phe Gly
        195                 200                 205

Ser Phe Pro Lys Leu Ile Met Thr Gln Val Ser Lys Ser Leu Gln Val
    210                 215                 220

Thr Arg Ile Phe Leu Gln Ala Leu Asn Leu Gly Ile Glu Val Ile Asn
225                 230                 235                 240

Thr Thr Asp His Leu Lys Phe Ser Lys Asp Cys Gly Arg Met Leu Thr
                245                 250                 255

Arg Met Trp Tyr Cys Ser Tyr Cys Gln Gly Leu Met Met Val Lys Pro
            260                 265                 270

Cys Gly Gly Tyr Cys Asn Val Val Met Gln Gly Cys Met Ala Gly Val
        275                 280                 285

Val Glu Ile Asp Lys Tyr Trp Arg Glu Tyr Ile Leu Ser Leu Glu Glu
    290                 295                 300

Leu Val Asn Gly Met Tyr Arg Ile Tyr Asp Met Glu Asn Val Leu Leu
305                 310                 315                 320

Gly Leu Phe Ser Thr Ile His Asp Ser Ile Gln Tyr Val Gln Lys Asn
                325                 330                 335

Gly Gly Lys Leu Thr Thr Thr Ile Gly Lys Leu Cys Ala His Ser Gln
            340                 345                 350

Gln Arg Gln Tyr Arg Ser Ala Tyr Tyr Pro Glu Asp Leu Phe Ile Asp
        355                 360                 365

Lys Lys Ile Leu Lys Val Ala His Val Glu His Glu Glu Thr Leu Ser
    370                 375                 380

Ser Arg Arg Arg Glu Leu Ile Gln Lys Leu Lys Ser Phe Ile Asn Phe
385                 390                 395                 400

Tyr Ser Ala Leu Pro Gly Tyr Ile Cys Ser His Ser Pro Val Ala Glu
                405                 410                 415

Asn Asp Thr Leu Cys Trp Asn Gly Gln Glu Leu Val Glu Arg Tyr Ser
            420                 425                 430
```

```
Gln Lys Ala Ala Arg Asn Gly Met Lys Asn Gln Phe Asn Leu His Glu
            435                 440                 445

Leu Lys Met Lys Gly Pro Glu Pro Val Val Ser Gln Ile Ile Asp Lys
450                 455                 460

Leu Lys His Ile Asn Gln Leu Leu Arg Thr Met Ser Val Pro Lys Gly
465                 470                 475                 480

Lys Val Leu Asp Lys Ser Leu Asp Glu Glu Gly Leu Glu Ser Gly Asp
                485                 490                 495

Cys Gly Asp Asp Glu Asp Glu Cys Ile Gly Ser Ser Gly Asp Gly Met
                500                 505                 510

Val Lys Val Lys Asn Gln Leu Arg Phe Leu Ala Glu Leu Ala Tyr Asp
            515                 520                 525

Leu Asp Val Asp Asp Ala Pro Gly Asn Ser Gln Gln Ala Thr Pro Lys
530                 535                 540

Asp Asn Glu Ile Ser Thr Phe His Asn Leu Gly Asn Val His Ser Pro
545                 550                 555                 560

Leu Lys Ile Leu Ile Ser Val Ala Ile Tyr Val Ala Cys Phe Phe Phe
                565                 570                 575

Leu Val His

<210> SEQ ID NO 12
<211> LENGTH: 239
<212> TYPE: PRT
<213> ORGANISM: Artificial sequence
<220> FEATURE:
<223> OTHER INFORMATION: Artificially synthesized sequence

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Asn Val Asn
            20                  25                  30

Ile Gly Trp Leu Gln Gln Lys Pro Gly Lys Ala Phe Lys Gly Leu Ile
        35                  40                  45

Tyr His Gly Lys Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Asn Gln Tyr Glu Asn Ile Pro Leu
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Gly Ser Asp Val Gln Leu Val
        115                 120                 125

Glu Ser Gly Gly Gly Leu Val Gln Pro Gly Gly Ser Leu Arg Leu Ser
    130                 135                 140

Cys Ala Val Ser Gly Tyr Ser Ile Thr Ser Asp Tyr Ala Trp Asn Trp
145                 150                 155                 160

Ile Arg Gln Ala Pro Gly Lys Gly Leu Glu Trp Leu Gly Tyr Ile Ser
                165                 170                 175

Tyr Arg Gly Arg Thr Gln Tyr Asn Pro Ser Leu Lys Ser Arg Ile Ser
            180                 185                 190

Ile Thr Arg Asp Asn Ser Lys Asn Thr Phe Phe Leu Gln Leu Asn Ser
        195                 200                 205

Leu Arg Ala Glu Asp Thr Ala Val Tyr Tyr Cys Ala Arg Met Gly Lys
```

Asn Trp Asp Tyr Trp Gly Gln Gly Thr Leu Val Thr Val Ser Ser
225                 230                 235

<210> SEQ ID NO 13
<211> LENGTH: 247
<212> TYPE: PRT
<213> ORGANISM: Artificial sequence
<220> FEATURE:
<223> OTHER INFORMATION: Artificially synthesized sequence

<400> SEQUENCE: 13

Gln Val Gln Leu Gln Glu Ser Gly Pro Gly Leu Ile Lys Pro Ser Gln
1               5                   10                  15

Thr Leu Ser Leu Thr Cys Thr Val Ser Gly Gly Ser Ile Ser Ser Gly
            20                  25                  30

Tyr Asn Trp His Trp Ile Arg Gln Pro Pro Gly Lys Gly Leu Glu Trp
        35                  40                  45

Ile Gly Tyr Ile His Tyr Thr Gly Ser Thr Asn Tyr Asn Pro Ala Leu
    50                  55                  60

Arg Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Ile Tyr Tyr Cys
                85                  90                  95

Ala Arg Ile Tyr Asn Gly Asn Ser Phe Pro Tyr Trp Gly Gln Gly Thr
            100                 105                 110

Thr Val Thr Val Ser Ser Gly Gly Gly Ser Gly Gly Gly Gly Ser
        115                 120                 125

Gly Gly Gly Gly Ser Asp Ile Val Met Thr Gln Ser Pro Asp Ser Leu
    130                 135                 140

Ala Val Ser Leu Gly Glu Arg Ala Thr Ile Asn Cys Lys Ser Ser Gln
145                 150                 155                 160

Ser Leu Phe Asn Ser Gly Asn Gln Lys Asn Tyr Leu Thr Trp Tyr Gln
                165                 170                 175

Gln Lys Pro Gly Gln Pro Pro Lys Leu Leu Ile Tyr Trp Ala Ser Thr
            180                 185                 190

Arg Glu Ser Gly Val Pro Asp Arg Phe Ser Gly Ser Gly Ser Gly Thr
        195                 200                 205

Asp Phe Thr Leu Thr Ile Ser Ser Leu Gln Ala Glu Asp Val Ala Val
    210                 215                 220

Tyr Tyr Cys Gln Asn Ala Tyr Ser Phe Pro Tyr Thr Phe Gly Gly Gly
225                 230                 235                 240

Thr Lys Leu Glu Ile Lys Arg
            245

<210> SEQ ID NO 14
<211> LENGTH: 243
<212> TYPE: PRT
<213> ORGANISM: Artificial sequence
<220> FEATURE:
<223> OTHER INFORMATION: Artificially synthesized sequence

<400> SEQUENCE: 14

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
            20                  25                  30

```
Glu Met His Trp Val Arg Gln Ala Pro Gly Gln Gly Leu Glu Trp Met
             35                  40                  45
Gly Ala Ile His Pro Gly Ser Gly Asp Thr Ala Tyr Asn Gln Arg Phe
 50                  55                  60
Lys Gly Arg Val Thr Ile Thr Ala Asp Lys Ser Thr Ser Thr Ala Tyr
 65                  70                  75                  80
Met Glu Leu Ser Ser Leu Arg Ser Glu Asp Thr Ala Val Tyr Tyr Cys
             85                  90                  95
Ala Arg Phe Tyr Ser Tyr Ala Tyr Trp Gly Gln Gly Thr Leu Val Thr
                100                 105                 110
Val Ser Ala Gly Gly Gly Gly Ser Gly Gly Gly Gly Ser Gly Gly Gly
            115                 120                 125
Gly Ser Asp Ile Val Met Thr Gln Thr Pro Leu Ser Leu Pro Val Thr
130                 135                 140
Pro Gly Glu Pro Ala Ser Ile Ser Cys Arg Ser Ser Gln Ser Leu Val
145                 150                 155                 160
His Ser Asn Gly Asn Thr Tyr Leu Gln Trp Tyr Leu Gln Lys Pro Gly
                165                 170                 175
Gln Ser Pro Gln Leu Leu Ile Tyr Lys Val Ser Asn Arg Phe Ser Gly
            180                 185                 190
Val Pro Asp Arg Phe Ser Gly Ser Gly Ser Gly Thr Asp Phe Thr Leu
        195                 200                 205
Lys Ile Ser Arg Val Glu Ala Glu Asp Val Gly Val Tyr Tyr Cys Ser
    210                 215                 220
Gln Ser Ile Tyr Val Pro Tyr Thr Phe Gly Gln Gly Thr Lys Leu Glu
225                 230                 235                 240
Ile Lys Arg

<210> SEQ ID NO 15
<211> LENGTH: 5
<212> TYPE: PRT
<213> ORGANISM: Artificial sequence
<220> FEATURE:
<223> OTHER INFORMATION: Artificially synthesized sequence

<400> SEQUENCE: 15

Asp Tyr Glu Met His
1               5

<210> SEQ ID NO 16
<211> LENGTH: 17
<212> TYPE: PRT
<213> ORGANISM: Artificial sequence
<220> FEATURE:
<223> OTHER INFORMATION: Artificially synthesized sequence

<400> SEQUENCE: 16

Ala Ile His Pro Gly Ser Gly Asp Thr Ala Tyr Asn Gln Arg Phe Lys
1               5                   10                  15
Gly

<210> SEQ ID NO 17
<211> LENGTH: 6
<212> TYPE: PRT
<213> ORGANISM: Artificial sequence
<220> FEATURE:
<223> OTHER INFORMATION: Artificially synthesized sequence

<400> SEQUENCE: 17
```

```
Phe Tyr Ser Tyr Ala Tyr
1               5
```

<210> SEQ ID NO 18
<211> LENGTH: 16
<212> TYPE: PRT
<213> ORGANISM: Artificial sequence
<220> FEATURE:
<223> OTHER INFORMATION: Artificially synthesized sequence

<400> SEQUENCE: 18

```
Arg Ser Ser Gln Ser Leu Val His Ser Asn Gly Asn Thr Tyr Leu Gln
1               5                   10                  15
```

<210> SEQ ID NO 19
<211> LENGTH: 7
<212> TYPE: PRT
<213> ORGANISM: Artificial sequence
<220> FEATURE:
<223> OTHER INFORMATION: Artificially synthesized sequence

<400> SEQUENCE: 19

```
Lys Val Ser Asn Arg Phe Ser
1               5
```

<210> SEQ ID NO 20
<211> LENGTH: 9
<212> TYPE: PRT
<213> ORGANISM: Artificial sequence
<220> FEATURE:
<223> OTHER INFORMATION: Artificially synthesized sequence

<400> SEQUENCE: 20

```
Ser Gln Ser Ile Tyr Val Pro Tyr Thr
1               5
```

<210> SEQ ID NO 21
<211> LENGTH: 356
<212> TYPE: PRT
<213> ORGANISM: Artificial sequence
<220> FEATURE:
<223> OTHER INFORMATION: Artificially synthesized sequence

<400> SEQUENCE: 21

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
            20                  25                  30

Glu Met His Trp Val Arg Gln Ala Pro Gly Gln Gly Leu Glu Trp Met
        35                  40                  45

Gly Ala Ile His Pro Gly Ser Gly Asp Thr Ala Tyr Asn Gln Arg Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Phe Tyr Ser Tyr Ala Tyr Trp Gly Gln Gly Thr Leu Val Thr
            100                 105                 110

Val Ser Ala Gly Gly Gly Gly Ser Gly Gly Gly Gly Ser Gly Gly Gly
        115                 120                 125

Gly Ser Asp Ile Val Met Thr Gln Thr Pro Leu Ser Leu Pro Val Thr
    130                 135                 140
```

Pro Gly Glu Pro Ala Ser Ile Ser Cys Arg Ser Ser Gln Ser Leu Val
145                 150                 155                 160

His Ser Asn Gly Asn Thr Tyr Leu Gln Trp Tyr Leu Gln Lys Pro Gly
            165                 170                 175

Gln Ser Pro Gln Leu Leu Ile Tyr Lys Val Ser Asn Arg Phe Ser Gly
            180                 185                 190

Val Pro Asp Arg Phe Ser Gly Ser Gly Ser Gly Thr Asp Phe Thr Leu
        195                 200                 205

Lys Ile Ser Arg Val Glu Ala Glu Asp Val Gly Val Tyr Tyr Cys Ser
        210                 215                 220

Gln Ser Ile Tyr Val Pro Tyr Thr Phe Gly Gln Gly Thr Lys Leu Glu
225                 230                 235                 240

Ile Lys Arg Arg Val Lys Phe Ser Arg Ser Ala Asp Ala Pro Ala Tyr
                245                 250                 255

Gln Gln Gly Gln Asn Gln Leu Tyr Asn Glu Leu Asn Leu Gly Arg Arg
                260                 265                 270

Glu Glu Tyr Asp Val Leu Asp Lys Arg Gly Arg Asp Pro Glu Met
            275                 280                 285

Gly Gly Lys Pro Gln Arg Arg Lys Asn Pro Gln Glu Gly Leu Tyr Asn
290                 295                 300

Glu Leu Gln Lys Asp Lys Met Ala Glu Ala Tyr Ser Glu Ile Gly Met
305                 310                 315                 320

Lys Gly Glu Arg Arg Arg Gly Lys Gly His Asp Gly Leu Tyr Gln Gly
                325                 330                 335

Leu Ser Thr Ala Thr Lys Asp Thr Tyr Asp Ala Leu His Met Gln Ala
                340                 345                 350

Leu Pro Pro Arg
        355

<210> SEQ ID NO 22
<211> LENGTH: 469
<212> TYPE: PRT
<213> ORGANISM: Artificial sequence
<220> FEATURE:
<223> OTHER INFORMATION: Artificially synthesized sequence

<400> SEQUENCE: 22

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
            20                  25                  30

Glu Met His Trp Val Arg Gln Ala Pro Gly Gln Gly Leu Glu Trp Met
        35                  40                  45

Gly Ala Ile His Pro Gly Ser Gly Asp Thr Ala Tyr Asn Gln Arg Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Phe Tyr Ser Tyr Ala Tyr Trp Gly Gln Gly Thr Leu Val Thr
            100                 105                 110

Val Ser Ala Gly Gly Gly Gly Ser Gly Gly Gly Gly Ser Gly Gly Gly
        115                 120                 125

Gly Ser Asp Ile Val Met Thr Gln Thr Pro Leu Ser Leu Pro Val Thr
    130                 135                 140

```
Pro Gly Glu Pro Ala Ser Ile Ser Cys Arg Ser Ser Gln Ser Leu Val
145                 150                 155                 160

His Ser Asn Gly Asn Thr Tyr Leu Gln Trp Tyr Leu Gln Lys Pro Gly
            165                 170                 175

Gln Ser Pro Gln Leu Leu Ile Tyr Lys Val Ser Asn Arg Phe Ser Gly
            180                 185                 190

Val Pro Asp Arg Phe Ser Gly Ser Gly Ser Gly Thr Asp Phe Thr Leu
        195                 200                 205

Lys Ile Ser Arg Val Glu Ala Glu Asp Val Gly Val Tyr Tyr Cys Ser
210                 215                 220

Gln Ser Ile Tyr Val Pro Tyr Thr Phe Gly Gln Gly Thr Lys Leu Glu
225                 230                 235                 240

Ile Lys Arg Thr Thr Thr Pro Ala Pro Arg Pro Pro Thr Pro Ala Pro
                245                 250                 255

Thr Ile Ala Ser Gln Pro Leu Ser Leu Arg Pro Glu Ala Cys Arg Pro
            260                 265                 270

Ala Ala Gly Gly Ala Val His Thr Arg Gly Leu Asp Phe Ala Cys Asp
        275                 280                 285

Phe Trp Val Leu Val Val Val Gly Gly Val Leu Ala Cys Tyr Ser Leu
290                 295                 300

Leu Val Thr Val Ala Phe Ile Ile Phe Trp Val Arg Ser Lys Arg Ser
305                 310                 315                 320

Arg Leu Leu His Ser Asp Tyr Met Asn Met Thr Pro Arg Arg Pro Gly
                325                 330                 335

Pro Thr Arg Lys His Tyr Gln Pro Tyr Ala Pro Pro Arg Asp Phe Ala
            340                 345                 350

Ala Tyr Arg Ser Arg Val Lys Phe Ser Arg Ser Ala Asp Ala Pro Ala
        355                 360                 365

Tyr Gln Gln Gly Gln Asn Gln Leu Tyr Asn Glu Leu Asn Leu Gly Arg
370                 375                 380

Arg Glu Glu Tyr Asp Val Leu Asp Lys Arg Arg Gly Arg Asp Pro Glu
385                 390                 395                 400

Met Gly Gly Lys Pro Gln Arg Arg Lys Asn Pro Gln Glu Gly Leu Tyr
                405                 410                 415

Asn Glu Leu Gln Lys Asp Lys Met Ala Glu Ala Tyr Ser Glu Ile Gly
            420                 425                 430

Met Lys Gly Glu Arg Arg Arg Gly Lys Gly His Asp Gly Leu Tyr Gln
        435                 440                 445

Gly Leu Ser Thr Ala Thr Lys Asp Thr Tyr Asp Ala Leu His Met Gln
450                 455                 460

Ala Leu Pro Pro Arg
465

<210> SEQ ID NO 23
<211> LENGTH: 466
<212> TYPE: PRT
<213> ORGANISM: Artificial sequence
<220> FEATURE:
<223> OTHER INFORMATION: Artificially synthesized sequence

<400> SEQUENCE: 23

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
            20                  25                  30
```

-continued

```
Glu Met His Trp Val Arg Gln Ala Pro Gly Gln Gly Leu Glu Trp Met
         35                  40                  45
Gly Ala Ile His Pro Gly Ser Gly Asp Thr Ala Tyr Asn Gln Arg Phe
 50                  55                  60
Lys Gly Arg Val Thr Ile Thr Ala Asp Lys Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Phe Tyr Ser Tyr Ala Tyr Trp Gly Gln Gly Thr Leu Val Thr
                100                 105                 110
Val Ser Ala Gly Gly Gly Gly Ser Gly Gly Gly Gly Ser Gly Gly Gly
            115                 120                 125
Gly Ser Asp Ile Val Met Thr Gln Thr Pro Leu Ser Leu Pro Val Thr
        130                 135                 140
Pro Gly Glu Pro Ala Ser Ile Ser Cys Arg Ser Ser Gln Ser Leu Val
145                 150                 155                 160
His Ser Asn Gly Asn Thr Tyr Leu Gln Trp Tyr Leu Gln Lys Pro Gly
                165                 170                 175
Gln Ser Pro Gln Leu Leu Ile Tyr Lys Val Ser Asn Arg Phe Ser Gly
            180                 185                 190
Val Pro Asp Arg Phe Ser Gly Ser Gly Ser Gly Thr Asp Phe Thr Leu
        195                 200                 205
Lys Ile Ser Arg Val Glu Ala Glu Asp Val Gly Val Tyr Tyr Cys Ser
    210                 215                 220
Gln Ser Ile Tyr Val Pro Tyr Thr Phe Gly Gln Gly Thr Lys Leu Glu
225                 230                 235                 240
Ile Lys Arg Thr Thr Thr Pro Ala Pro Arg Pro Pro Thr Pro Ala Pro
                245                 250                 255
Thr Ile Ala Ser Gln Pro Leu Ser Leu Arg Pro Glu Ala Cys Arg Pro
            260                 265                 270
Ala Ala Gly Gly Ala Val His Thr Arg Gly Leu Asp Phe Ala Cys Asp
        275                 280                 285
Ile Tyr Ile Trp Ala Pro Leu Ala Gly Thr Cys Gly Val Leu Leu Leu
    290                 295                 300
Ser Leu Val Ile Thr Leu Tyr Cys Lys Arg Gly Arg Lys Lys Leu Leu
305                 310                 315                 320
Tyr Ile Phe Lys Gln Pro Phe Met Arg Pro Val Gln Thr Thr Gln Glu
                325                 330                 335
Glu Asp Gly Cys Ser Cys Arg Phe Pro Glu Glu Glu Glu Gly Gly Cys
            340                 345                 350
Glu Leu Arg Val Lys Phe Ser Arg Ser Ala Asp Ala Pro Ala Tyr Lys
        355                 360                 365
Gln Gly Gln Asn Gln Leu Tyr Asn Glu Leu Asn Leu Gly Arg Arg Glu
    370                 375                 380
Glu Tyr Asp Val Leu Asp Lys Arg Gly Arg Asp Pro Glu Met Gly
385                 390                 395                 400
Gly Lys Pro Arg Arg Lys Asn Pro Gln Glu Gly Leu Tyr Asn Glu Leu
                405                 410                 415
Gln Lys Asp Lys Met Ala Glu Ala Tyr Ser Glu Ile Gly Met Lys Gly
            420                 425                 430
Glu Arg Arg Arg Gly Lys Gly His Asp Gly Leu Tyr Gln Gly Leu Ser
        435                 440                 445
Thr Ala Thr Lys Asp Thr Tyr Asp Ala Leu His Met Gln Ala Leu Pro
```

```
                450                 455                 460

Pro Arg
465

<210> SEQ ID NO 24
<211> LENGTH: 511
<212> TYPE: PRT
<213> ORGANISM: Artificial sequence
<220> FEATURE:
<223> OTHER INFORMATION: Artificially synthesized sequence

<400> SEQUENCE: 24

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
            20                  25                  30

Glu Met His Trp Val Arg Gln Ala Pro Gly Gln Gly Leu Glu Trp Met
        35                  40                  45

Gly Ala Ile His Pro Gly Ser Gly Asp Thr Ala Tyr Asn Gln Arg Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Phe Tyr Ser Tyr Ala Tyr Trp Gly Gln Gly Thr Leu Val Thr
            100                 105                 110

Val Ser Ala Gly Gly Gly Gly Ser Gly Gly Gly Gly Ser Gly Gly Gly
        115                 120                 125

Gly Ser Asp Ile Val Met Thr Gln Thr Pro Leu Ser Leu Pro Val Thr
    130                 135                 140

Pro Gly Glu Pro Ala Ser Ile Ser Cys Arg Ser Ser Gln Ser Leu Val
145                 150                 155                 160

His Ser Asn Gly Asn Thr Tyr Leu Gln Trp Tyr Leu Gln Lys Pro Gly
                165                 170                 175

Gln Ser Pro Gln Leu Leu Ile Tyr Lys Val Ser Asn Arg Phe Ser Gly
            180                 185                 190

Val Pro Asp Arg Phe Ser Gly Ser Gly Ser Gly Thr Asp Phe Thr Leu
        195                 200                 205

Lys Ile Ser Arg Val Glu Ala Glu Asp Val Gly Val Tyr Tyr Cys Ser
    210                 215                 220

Gln Ser Ile Tyr Val Pro Tyr Thr Phe Gly Gln Gly Thr Lys Leu Glu
225                 230                 235                 240

Ile Lys Arg Thr Thr Thr Pro Ala Pro Arg Pro Pro Thr Pro Ala Pro
                245                 250                 255

Thr Ile Ala Ser Gln Pro Leu Ser Leu Arg Pro Glu Ala Cys Arg Pro
            260                 265                 270

Ala Ala Gly Gly Ala Val His Thr Arg Gly Leu Asp Phe Ala Cys Asp
        275                 280                 285

Phe Trp Val Leu Val Val Val Gly Gly Val Leu Ala Cys Tyr Ser Leu
    290                 295                 300

Leu Val Thr Val Ala Phe Ile Ile Phe Trp Val Arg Ser Lys Arg Ser
305                 310                 315                 320

Arg Leu Leu His Ser Asp Tyr Met Asn Met Thr Pro Arg Arg Pro Gly
                325                 330                 335

Pro Thr Arg Lys His Tyr Gln Pro Tyr Ala Pro Pro Arg Asp Phe Ala
```

```
                    340                 345                 350
Ala Tyr Arg Ser Lys Arg Gly Arg Lys Lys Leu Leu Tyr Ile Phe Lys
            355                 360                 365

Gln Pro Phe Met Arg Pro Val Gln Thr Thr Gln Glu Glu Asp Gly Cys
    370                 375                 380

Ser Cys Arg Phe Pro Glu Glu Glu Gly Gly Cys Glu Leu Arg Val
385                 390                 395                 400

Lys Phe Ser Arg Ser Ala Asp Ala Pro Ala Tyr Gln Gln Gly Gln Asn
                405                 410                 415

Gln Leu Tyr Asn Glu Leu Asn Leu Gly Arg Arg Glu Glu Tyr Asp Val
            420                 425                 430

Leu Asp Lys Arg Arg Gly Arg Asp Pro Glu Met Gly Gly Lys Pro Gln
        435                 440                 445

Arg Arg Lys Asn Pro Gln Glu Gly Leu Tyr Asn Glu Leu Gln Lys Asp
    450                 455                 460

Lys Met Ala Glu Ala Tyr Ser Glu Ile Gly Met Lys Gly Glu Arg Arg
465                 470                 475                 480

Arg Gly Lys Gly His Asp Gly Leu Tyr Gln Gly Leu Ser Thr Ala Thr
                485                 490                 495

Lys Asp Thr Tyr Asp Ala Leu His Met Gln Ala Leu Pro Pro Arg
            500                 505                 510
```

COMBINATION OF CELLULAR IMMUNOTHERAPY

RELATED INFORMATION PARAGRAPH

This application is a 35 U.S.C. 371 national stage filing of International Application No. PCT/CN2019/074535, filed on Feb. 2, 2019, which claims the benefit of the priority date of Chinese Application No. CN201910008444.2, filed on Jan. 4, 2019, Chinese Application No. CN201810129611.4, filed on Feb. 8, 2018 and Chinese Application No. CN201810107786.5, filed on Feb. 2, 2018, the content of each of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Oct. 1, 2020, is named BCLS-011US_Sequence_Listing.txt and is 32,749 bytes in size.

FIELD OF THE INVENTION

The invention belongs to the field of cellular immunotherapy, and particularly relates to the combination of an immune effector cell and a kinase inhibitor chemotherapeutic agent for anti-tumor therapy.

BACKGROUND TECHNIQUE

In recent years, cellular immunotherapy such as CAR-T cell therapy has shown amazing therapeutic effect in the treatment of blood tumor. At present, more than 200 CAR-T cells have been used in clinical trials of blood tumor treatment (Clinical development of CAR T cells-challenges and opportunities in translating innovative treatment concepts, Jessica Hartmann et al., EMBO Molecule Medicine, Published on line, Aug. 1, 2017). However, the treatment of solid tumors is difficult to achieve the effect of blood tumor treatment.

This is because for blood tumors, CAR-T cells can more easily reach tumor cells through intravenous infusion to achieve killing, while it is more difficult for CAR-T cells to home to the tumor tissue of a solid tumor. In addition, solid tumors usually have a complex and dynamic tumor microenvironment that can enable tumor cells, benign cells, stromal cells, and vascular cells, etc. to interact with each other. Moreover, there is also a network of interaction between cytokines and growth factors in the tumor microenvironment. Therefore, when CAR-T therapy is used in the treatment of solid tumors, the efficacy is usually poor.

SUMMARY OF THE INVENTION

The object of the present invention is to provide a method for treating a tumor, so as to improve the application effect of cellular immunotherapy, especially CAR-T cell therapy, in solid tumors.

In the first aspect of the present invention, provided is a method for treating a tumor, wherein an immune effector cell and a second therapeutic agent are administered to an individual suffering from a tumor, the immune effector cell expresses a receptor recognizing a tumor antigen, and the second therapeutic agent is a kinase inhibitor.

In a particular embodiment, the second therapeutic agent is a compound of formula I, or a pharmaceutically acceptable salt thereof,

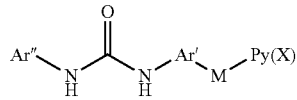

I wherein Ar' is an unsubstituted or substituted phenyl, and the substituent is selected from halogen and C1-10 alkyl, M is one or more bridging groups selected from —O— or —S—, Py(X) is X-substituted pyridyl, X is —C(O)R$_x$, wherein R$_x$ is NR$_a$R$_b$, and each of R$_a$ and R$_b$ is:
 a) hydrogen,
 b) C1-10 alkyl,
 c) C1-10 alkyl substituted by hydroxy,
 d) C3-12 cycloalkyl containing 1-3 N, S or O heteroatoms, or
 e) —OSi(R$_f$)3, wherein R$_f$ is C1-10 alkyl, Ar" is unsubstituted or substituted phenyl, and the substituent is selected from halogen or Wn, wherein n=0-3, and W is selected from:
 a) C1-10 alkyl,
 b) C1-10 alkoxy,
 c) C1-10 haloalkyl, and
 d) C3-12 heteroaryl containing 1-3 N, S or O heteroatoms, and the heteroaryl may be substituted by C1-10 alkyl.

In the second aspect of the present invention, also provided is a method for reducing the growth, survival or viability of cancer cells, characterized in that an immune effector cell and a second therapeutic agent are administered to an individual suffering from a tumor, wherein the immune effector cell expresses a receptor recognizing a tumor antigen, and the second therapeutic agent is a compound of formula I, or a pharmaceutically acceptable salt thereof,

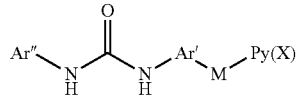

I wherein Ar' is an unsubstituted or substituted phenyl, and the substituent is selected from halogen and C1-10 alkyl, M is one or more bridging groups selected from —O— or —S—, Py(X) is X-substituted pyridyl, X is —C(O)R$_x$, wherein R$_x$ is NR$_a$R$_b$, and each of R$_a$ and R$_b$ is:
 a) hydrogen,
 b) C1-10 alkyl,
 c) C1-10 alkyl substituted by hydroxy,
 d) C3-12 cycloalkyl containing 1-3 N, S or O heteroatoms, and
 e) —OSi(R$_f$)3, wherein R$_f$ is C1-10 alkyl, Ar" is unsubstituted or substituted phenyl, and the substituent is selected from halogen or Wn, wherein n=0-3, and W is selected from:
 a) C1-10 alkyl,
 b) C1-10 alkoxy, c) C1-10 haloalkyl, and
d) C3-12 heteroaryl containing 1-3 N, S or O heteroatoms, and the heteroaryl may be substituted by C1-10 alkyl.

In a preferred embodiment, the above-mentioned method for treating a tumor, or the method for reducing the growth, survival or viability of cancer cells is adopted, and the individual is not subjected to lymphocyte clearance before administering the immune effector cell to the individual suffering from a tumor.

In a preferred embodiment, when the above method for treating a tumor, or the method for reducing the growth, survival or viability of cancer cells is adopted, the therapeutic effect of the immune effector cell and the second therapeutic agent is greater than the effect of either the immune effector cell or the second therapeutic agent used alone.

In another preferred embodiment, the Ar" is substituted phenyl, and the substituent is selected from any one of chlorine, bromine, fluorine, trifluoromethyl, methoxy and tert-butyl, or a combination thereof.

In another preferred embodiment, the M is —O—.

In another preferred embodiment, each of the $R_a$ and $R_b$ is H or C1-10 alkyl, preferably $R_a$ and $R_b$ are H and methyl, respectively.

In another preferred embodiment, the pharmaceutically acceptable salt is selected from: a) a basic salt of inorganic acid and organic acid, and the acids are selected from: hydrochloric acid, hydrobromic acid, sulfuric acid, phosphoric acid, methanesulfonic acid, trifluoromethanesulfonic acid, benzenesulfonic acid, p-toluenesulfonic acid, 1-naphthalenesulfonic acid, 2-naphthalenesulfonic acid, acetic acid, trifluoroacetic acid, malic acid, tartaric acid, citric acid, lactic acid, oxalic acid, succinic acid, fumaric acid, maleic acid, benzoic acid, salicylic acid, phenylacetic acid, and mandelic acid; b) an acid salt of organic base and inorganic base, and the cations are selected from: alkali metal cations, alkaline earth metal cations, ammonium cations, aliphatic-substituted ammonium cations, and aromatic-substituted ammonium cations.

In a particular embodiment, the second therapeutic agent is selected from any of the following compounds or a pharmaceutically acceptable salt thereof:
N-(2-methoxy-(5-trifluoromethyl)phenyl)-N'-(3-(2-carbamoyl-4-pyridyloxy)phenyl)urea,
N-(2-methoxy-(5-trifluoromethyl)phenyl)-N'-(3-(2-(N-methylcarbamoyl)-4-pyridyloxy)phenyl)urea,
N-(2-methoxy-(5-trifluoromethyl)phenyl)-N'-(4-(2-carbamoyl-4-pyridyloxy)phenyl)urea,
N-(2-methoxy-(5-trifluoromethyl)phenyl)-N'-(4-(2-(N-methylcarbamoyl)-4-pyridyloxy)phenyl)urea,
N-(2-methoxy-(5-trifluoromethyl)phenyl)-N'-(4-(2-(N-methylcarbamoyl)-4-pyridylthio)phenyl)urea,
N-(2-methoxy-(5-trifluoromethyl)phenyl)-N'-(2-chloro-4-(2-(N-methylcarbamoyl)(4-pyridyloxy))phenyl)urea,
N-(2-methoxy-(5-trifluoromethyl)phenyl)-N'-(3-chloro-4-(2-(N-methylcarbamoyl)(4-pyridyloxy))phenyl)urea,
N-(4-chloro-3-(trifluoromethyl)phenyl)-N'-(3-(2-carbamoyl-4-pyridyloxy)phenyl)urea,
N-(4-chloro-3-(trifluoromethyl)phenyl)-N'-(3-(2-(N-methylcarbamoyl)-4-pyridyloxy)phenyl)urea,
N-(4-chloro-3-(trifluoromethyl)phenyl)-N'-(4-(2-carbamoyl-4-pyridyloxy)phenyl)urea,
N-(4-chloro-3-(trifluoromethyl)phenyl)-N'-(4-(2-(N-methylcarbamoyl)-4-pyridyloxy)phenyl)urea,
N-(4-chloro-3-(trifluoromethyl)phenyl)-N'-2-fluoro-(4-(2-(N-methylcarbamoyl)-4-pyridyloxy)phenyl)urea,
N-(4-bromo-3-(trifluoromethyl)phenyl)-N'-(3-(2-(N-methylcarbamoyl)-4-pyridyloxy)phenyl)urea,
N-(4-bromo-3-(trifluoromethyl)phenyl)-N'-(4-(2-(N-methylcarbamoyl)-4-pyridyloxy)phenyl)urea,
N-(4-bromo-3-(trifluoromethyl)phenyl)-N'-(3-(2-(N-methylcarbamoyl)-4-pyridylthio)phenyl)urea,
N-(4-bromo-3-(trifluoromethyl)phenyl)-N'-(2-chloro-4-(2-(N-methylcarbamoyl)(4-pyridyloxy))phenyl)urea,
N-(4-bromo-3-(trifluoromethyl)phenyl)-N'-(3-chloro-4-(2-(N-methylcarbamoyl)(4-pyridyloxy))phenyl)urea,
N-(2-methoxy-4-chloro-5-(trifluoromethyl)phenyl)-N'-(3-(2-(N-methylcarbamoyl)-4-pyridyloxy)phenyl)urea,
N-(2-methoxy-4-chloro-5-(trifluoromethyl)phenyl)-N'-(4-(2-(N-methylcarbamoyl)-4-pyridyloxy)phenyl)urea,
N-(2-methoxy-4-chloro-5-(trifluoromethyl)phenyl)-N'-(2-chloro-4-(2-(N-methylcarbamoyl)(4-pyridyloxy))phenyl)urea,
N-(2-methoxy-4-chloro-5-(trifluoromethyl)phenyl)-N'-(3-chloro-4-(2-(N-methylcarbamoyl)(4-pyridyloxy))phenyl)urea.

In a particular embodiment, the second therapeutic agent is selected from the following compound of formula II or formula III, or a pharmaceutically acceptable salt thereof:

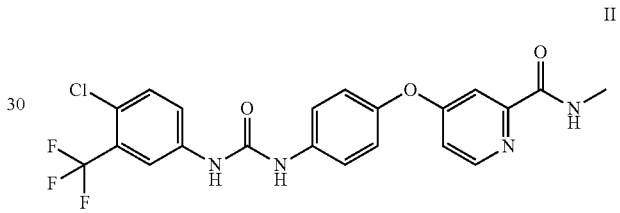

II

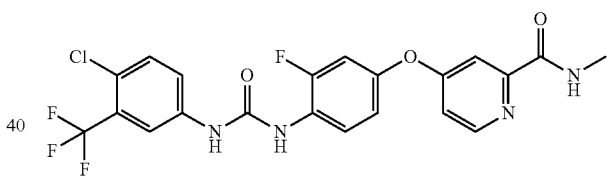

III

In a particular embodiment, the pharmaceutically acceptable salt of the second therapeutic agent is selected from: tosylate, benzenesulfonate, hydrochloride, and methanesulfonate.

In a particular embodiment, the second therapeutic agent is a compound of formula II, or a hydrate, preferably a monohydrate of a compound of formula II.

In another preferred embodiment, for the individual subject, the second therapeutic agent is administered 100-1000 mg per day, preferably 200-800 mg per day, and more preferably 400-800 mg per day, In another preferred embodiment, for the individual subject, the second therapeutic agent is administered 1-3 times per day, and preferably the second therapeutic agent is administered twice per day.

In another preferred embodiment, for the individual subject, the dose of the immune effector cell per administration is about $1 \times 10^5 - 1 \times 10^8$ cells/kg subject weight, and more preferably the dose per administration is about $1 \times 10^5 - 1 \times 10^7$ cells/kg subject weight.

In another preferred embodiment, the immune effector cell and the second therapeutic agent are administered in no particular order; the second therapeutic agent may be administered first and then the immune effector cell; or they may be administered simultaneously; the immune effector cell may also be administered first and then the second therapeutic agent, and preferably the immune effector cell is administrated during the administration of the second therapeutic agent.

In a particular embodiment, the second therapeutic agent is administered orally.

In another preferred embodiment, the receptor is selected from: chimeric antigen receptor (CAR), T cell receptor (TCR), T cell fusion protein (TFP), T cell antigen coupler (TAC), or a combination thereof.

In a particular embodiment, the chimeric antigen receptor comprises:
  (i) an antibody or a fragment thereof that specifically recognizes a tumor antigen, the transmembrane region of CD28 or CD8, the co-stimulatory signal domain of CD28, and the intracellular domain of CD3ζ; or
  (ii) an antibody or a fragment thereof that specifically recognizes a tumor antigen, the transmembrane region of CD28 or CD8, the co-stimulatory signal domain of CD137, and the intracellular domain of CD3ζ; or
  (iii) an antibody or a fragment thereof that specifically recognizes a tumor antigen, the transmembrane region of CD28 or CD8, the co-stimulatory signal domain of CD28, the co-stimulatory signal domain of CD137, and the intracellular domain of CD3ζ.

In a particular embodiment, the tumor antigen is selected from: thyroid stimulating hormone receptor (TSHR); CD171; CS-1; C-type lectin-like molecule-1; ganglioside GD3; Tn antigen; CD19; CD20; CD22; CD30; CD70; CD123; CD138; CD33; CD44; CD44v7/8; CD38; CD44v6; B7H3(CD276); B7H6; KIT(CD117); interleukin 13 receptor subunit α (IL-13Rα); interleukin 11 receptor α (IL-11Rα); prostate stem cell antigen (PSCA); prostate specific membrane antigen (PSMA); carcinoembryonic antigen (CEA); NY-ESO-1; HIV-1 Gag; MART-1; gp100; tyrosinase; mesothelin; EpCAM; protease serine 21 (PRSS21); vascular endothelial growth factor receptor; Lewis (Y) antigen; CD24; platelet derived growth factor receptor β (PDGFR-β); stage-specific embryonic antigen-4 (SSEA-4); cell surface-associated mucin 1 (MUC1); MUC6; epidermal growth factor receptor family and its mutants (EGFR, EGFR2, ERBB3, ERBB4, EGFRvIII); neural cell adhesion molecule (NCAM); carbonic anhydrase IX (CAIX); LMP2; ephrin A receptor 2 (EphA2); fucosyl GM1; sialyl Lewis adhesion molecule (sLe); ganglioside GM3 (aNeu5Ac(2-3)bDGalp(1-4)bDGlcp(1-1)Cer; TGS5; high molecular weight melanoma associated antigen (HMWMAA); o-acetyl GD2 ganglioside (OAcGD2); folate receptor; tumor vascular endothelial marker 1 (TEM1/CD248); tumor vascular endothelial marker 7 related (TEM7R); claudin 6, claudin 18.2, claudin 18.1; ASGPR1; CDH16; 5T4; 8H9; αvβ6 integrin; B cell maturation antigen (BCMA); CA9; kappa light chain; CSPG4; EGP2, EGP40; FAP; FAR; FBP; embryonic AchR; HLA-A1, HLA-A2; MAGEA1, MAGE3; KDR; MCSP; NKG2D ligand; PSC1; ROR1; Sp7; SURVIVIN; TAG72; TEM1; fibronectin; tenascin; carcinoembryonic variant of tumor necrosis zone; G protein-coupled receptor family C group 5 member D (GPRC5D); X chromosome open reading frame 61 (CXORF61); CD97; CD179a; anaplastic lymphoma kinase (ALK); polysialic acid; placenta-specific 1 (PLAC1); hexose part of globoH glycoceramide (GloboH); breast differentiation antigen (NY-BR-1); uroplakin 2 (UPK2); hepatitis A virus cell receptor 1 (HAVCRi); adrenaline receptor 3 (ADRB3); pannexin 3 (PANX3); G protein coupled receptor 20 (GPR20); lymphocyte antigen 6 complex locus K9 (LY6K); olfactory receptor 51E2 (OR51E2); TCRγ alternate reading frame protein (TARP); Wilms tumor protein (WT1); ETS translocation variant gene 6 (ETV6-AML); sperm protein 17 (SPA17); X antigen family member 1A (XAGE1); angiopoietin binding cell surface receptor 2 (Tie2); melanoma cancer testis antigen-1 (MAD-CT-1); melanoma cancer testis antigen-2 (MAD-CT-2); Fos-related antigen 1; p53 mutant; human telomerase reverse transcriptase (hTERT); sarcoma translocation breakpoint; melanoma inhibitor of apoptosis (ML-IAP); ERG (transmembrane protease serine 2 (TMPRSS2) ETS fusion gene); N-acetylglucosamine transferase V (NA17); paired box protein Pax-3 (PAX3); androgen receptor; cyclin Bi; V-myc avian myelocytomatosis viral oncogene neuroblastoma-derived homolog (MYCN); Ras homolog family member C (RhoC); cytochrome P450 1B1 (CYP1B1); CCCTC binding factor (zinc finger protein)-like (BORIS); squamous cell carcinoma antigen 3 (SART3) recognized by T cells; paired box protein Pax-5 (PAX5); proacrosin binding protein sp32 (OYTES); lymphocyte specific protein tyrosine kinase (LCK); A-kinase anchoring protein 4 (AKAP-4); synovial sarcoma X breakpoint 2 (SSX2); CD79a; CD79b; CD72; leukocyte-associated immunoglobulin-like receptor 1 (LAIR1); Fc fragment of IgA receptor (FCAR); leukocyte immunoglobulin-like receptor subfamily member 2 (LILRA2); CD300 molecular-like family member f (CD300LF); C-type lectin domain family 12 member A (CLEC12A); bone marrow stromal cell antigen 2 (BST2); EGF-like module containing mucin-like hormone receptor-like 2 (EMR2); lymphocyte antigen 75 (LY75); glypican-3 (GPC3); Fc receptor-like 5 (FCRL5); immunoglobulin lambda-like polypeptide 1 (IGLL1).

In a particular embodiment, the tumor antigen is a solid tumor antigen. Preferably, the solid tumor antigen is vascular endothelial growth factor receptor, EGFR, EGFRvIII, GPC3, or claudin 18.2. More preferably, the solid tumor antigen is GPC3, EGFR, EGFRvIII, or vascular endothelial growth factor receptor.

In a particular embodiment, the vascular endothelial growth factor receptor is vascular endothelial growth factor receptor 2 (VEGFR2).

In a particular embodiment, the solid tumor antigen is GPC3.

In a particular embodiment, the antibody specifically recognizing a tumor antigen is an antibody targeting glypican-3 (GPC3).

In a preferred embodiment, the antibody specifically recognizing a tumor antigen comprises HCDR1, HCDR2, HCDR3 respectively represented by SEQ ID NOs: 15, 16, 17, and LCDR1, LCDR2, LCDR3 respectively represented by SEQ ID NOs: 18, 19, 20.

In a particular embodiment, the amino acid sequence of the antibody specifically recognizing the tumor antigen has at least 90% identity with the sequence of SEQ ID NO: 14.

In a particular embodiment, the amino acid sequence of the chimeric antigen receptor has at least 90% identity with the sequence of SEQ ID NO: 21, 22, 23 or 24.

In a preferred embodiment, the treatment is determined by the following clinical outcome or a combination thereof: increased, enhanced, or prolonged anti-tumor activity of the immune effector cell; increased number of anti-tumor immune effector cells or the activated immune effector cells as compared with the number before treatment.

In a particular embodiment, the clinical outcome is selected from: tumor regression; tumor shrinkage; tumor necrosis; anti-tumor response through the immune system; tumor expansion, recurrence or spread or a combination thereof.

In a particular embodiment, the therapeutic effect is predicted by: the presence of immune effector cells, or the presence of genetic markers indicative of T cell inflammation, or a combination thereof; preferably by detecting changes in the levels of IFN-γ and TNFα.

In a particular embodiment, tumor comprises: breast cancer, glioma, blood cancer, colon cancer, rectal cancer, renal cell carcinoma, liver cancer, lung cancer, small intestine cancer, esophageal cancer, melanoma, bone cancer, pancreatic cancer, skin cancer, head and neck cancer, skin or intraocular malignant melanoma, uterine cancer, ovarian cancer, rectal cancer, anal cancer, stomach cancer, testicular cancer, uterine cancer, fallopian tube cancer, endometrial cancer, cervical cancer, vagina cancer, vulva cancer, Hodgkin's disease, non-Hodgkin's lymphoma, endocrine system cancer, thyroid cancer, parathyroid cancer, adrenal cancer, soft tissue sarcoma, urethral cancer, penile cancer, childhood solid tumor, bladder cancer, renal or ureteral cancer, renal pelvis cancer, central nervous system (CNS) tumor, primary CNS lymphoma, tumor angiogenesis, spinal tumor, brainstem glioma, pituitary adenoma, Kaposi's sarcoma, epidermoid carcinoma, squamous cell carcinoma, T-cell lymphoma, environmentally induced cancer, a combination of the cancers, and the metastatic foci of the cancer. Preferably, the tumor is selected from liver cancer, renal cell carcinoma, squamous cell lung carcinoma, and thyroid cancer.

In a particular embodiment, the immune effector cell include: T cell, B cell, natural killer cell (NK cell), natural killer T cell (NKT cell), mastocyte, or bone marrow-derived phagocyte, or a combination thereof; preferably, the immune effector cell is selected from autologous T cell, allogeneic T cell, or allogeneic NK cell; and more preferably, the T cell is an autologous T cell.

In the third aspect of the present invention, the present invention provides a drug delivery system comprising an immune effector cell and a second therapeutic agent, wherein the immune effector cell expresses a receptor recognizing a tumor antigen.

The second therapeutic agent is a compound of formula I, or a pharmaceutically acceptable salt thereof, $$Ar''\underset{H}{N}\underset{H}{\overset{O}{\underset{\|}{C}}}N\overset{Ar'}{\diagdown}M\diagdown Py(X)$$

I wherein Ar' is an unsubstituted or substituted phenyl, and the substituent is selected from halogen and C1-10 alkyl, M is one or more bridging groups selected from —O— or —S—, Py(X) is X-substituted pyridyl, X is —C(O)$R_x$, wherein $R_x$ is $NR_aR_b$, and each of $R_a$ and $R_b$ is:
a) hydrogen,
b) C1-10 alkyl,
c) C1-10 alkyl substituted by hydroxy,
d) C3-12 cycloalkyl containing 1-3 N, S or O heteroatoms, or
e) —OSi($R_f$)3, wherein Reis C1-10 alkyl, Ar" is unsubstituted or substituted phenyl, and the substituent is selected from halogen or Wn, wherein n=0-3, and W is selected from:
a) C1-10 alkyl,
b) C1-10 alkoxy,
c) C1-10 haloalkyl, and
d) C3-12 heteroaryl containing 1-3 N, S or O heteroatoms, and the heteroaryl may be substituted by C1-10 alkyl.

In a preferred embodiment, the Ar" is a substituted phenyl, and the substituent is selected from any one of chlorine, bromine, fluorine, trifluoromethyl, methoxy and tert-butyl, or a combination thereof.

In another preferred embodiment, the M is —O—.

In another preferred embodiment, each of the $R_a$ and $R_b$ is H or C1-10 alkyl. Preferably $R_a$ and $R_b$ are H and methyl, respectively.

In another preferred embodiment, the pharmaceutically acceptable salt is selected from: a) a basic salt of inorganic acid and organic acid, and the acids are selected from: hydrochloric acid, hydrobromic acid, sulfuric acid, phosphoric acid, methanesulfonic acid, trifluoromethanesulfonic acid, benzenesulfonic acid, p-toluenesulfonic acid, 1-naphthalenesulfonic acid, 2-naphthalenesulfonic acid, acetic acid, trifluoroacetic acid, malic acid, tartaric acid, citric acid, lactic acid, oxalic acid, succinic acid, fumaric acid, maleic acid, benzoic acid, salicylic acid, phenylacetic acid, and mandelic acid; b) an acid salt of organic base and inorganic base, and the cations are selected from: alkali metal cations, alkaline earth metal cations, ammonium cations, aliphatic-substituted ammonium cations, and aromatic-substituted ammonium cations.

In a particular embodiment, the second therapeutic agent is selected from any of the following compounds or a pharmaceutically acceptable salt thereof:
N-(2-methoxy-(5-trifluoromethyl)phenyl)-N'-(3-(2-carbamoyl-4-pyridyloxy)phenyl)urea,
N-(2-methoxy-(5-trifluoromethyl)phenyl)-N'-(3-(2-(N-methylcarbamoyl)-4-pyridyloxy)phenyl)urea,
N-(2-methoxy-(5-trifluoromethyl)phenyl)-N'-(4-(2-carbamoyl-4-pyridyloxy)phenyl)urea,
N-(2-methoxy-(5-trifluoromethyl)phenyl)-N'-(4-(2-(N-methylcarbamoyl)-4-pyridyloxy)phenyl)urea,
N-(2-methoxy-(5-trifluoromethyl)phenyl)-N'-(4-(2-(N-methylcarbamoyl)-4-pyridylthio)phenyl)urea,
N-(2-methoxy-(5-trifluoromethyl)phenyl)-N'-(2-chloro-4-(2-(N-methylcarbamoyl)(4-pyridyloxy))phenyl)urea,
N-(2-methoxy-(5-trifluoromethyl)phenyl)-N'-(3-chloro-4-(2-(N-methylcarbamoyl)(4-pyridyloxy))phenyl)urea,
N-(4-chloro-3-(trifluoromethyl)phenyl)-N'-(3-(2-carbamoyl-4-pyridyloxy)phenyl)urea,
N-(4-chloro-3-(trifluoromethyl)phenyl)-N'-(3-(2-(N-methylcarbamoyl)-4-pyridyloxy)phenyl)urea,
N-(4-chloro-3-(trifluoromethyl)phenyl)-N'-(4-(2-carbamoyl-4-pyridyloxy)phenyl)urea,
N-(4-chloro-3-(trifluoromethyl)phenyl)-N'-(4-(2-(N-methylcarbamoyl)-4-pyridyloxy)phenyl)urea,
N-(4-chloro-3-(trifluoromethyl)phenyl)-N'-2-fluoro-(4-(2-(N-methylcarbamoyl)-4-pyridyloxy)phenyl)urea,
N-(4-bromo-3-(trifluoromethyl)phenyl)-N'-(3-(2-(N-methylcarbamoyl)-4-pyridyloxy)phenyl)urea,
N-(4-bromo-3-(trifluoromethyl)phenyl)-N'-(4-(2-(N-methylcarbamoyl)-4-pyridyloxy)phenyl)urea,
N-(4-bromo-3-(trifluoromethyl)phenyl)-N'-(3-(2-(N-methylcarbamoyl)-4-pyridylthio)phenyl)urea,
N-(4-bromo-3-(trifluoromethyl)phenyl)-N'-(2-chloro-4-(2-(N-methylcarbamoyl)(4-pyridyloxy))phenyl)urea,
N-(4-bromo-3-(trifluoromethyl)phenyl)-N'-(3-chloro-4-(2-(N-methylcarbamoyl)(4-pyridyloxy))phenyl)urea,
N-(2-methoxy-4-chloro-5-(trifluoromethyl)phenyl)-N'-(3-(2-(N-methylcarbamoyl)-4-pyridyloxy)phenyl)urea,
N-(2-methoxy-4-chloro-5-(trifluoromethyl)phenyl)-N'-(4-(2-(N-methylcarbamoyl)-4-pyridyloxy)phenyl)urea, N-(2-methoxy-4-chloro-5-(trifluoromethyl)phenyl)-N'-(2-chloro-4-(2-(N-methylcarbamoyl)(4-pyridyloxy))phenyl)urea, N-(2-methoxy-4-chloro-5-(trifluoromethyl)phenyl)-N'-(3-chloro-4-(2-(N-methylcarbamoyl)(4-pyridyloxy))phenyl)urea.

In a particular embodiment, the second therapeutic agent is selected from the following compound of formula II or formula III, or a pharmaceutically acceptable salt thereof:

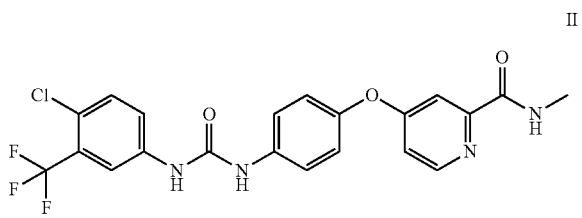 [SMILES: CNC(=O)c1cc(Oc2ccc(NC(=O)Nc3ccc(Cl)c(C(F)(F)F)c3)cc2)ccn1]

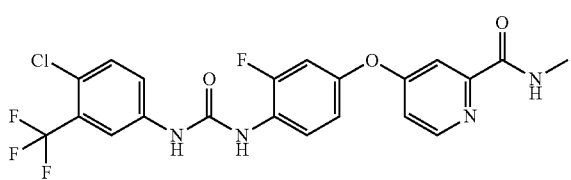

The chemical names of the compounds of formula II or formula III are:

N-(4-chloro-3-(trifluoromethyl)phenyl)-N'-(3-(2-(N-methylcarbamoyl)-4-pyridyloxy)phenyl)urea, and N-(4-chloro-3-(trifluoromethyl)phenyl)-N'-2-fluoro-(4-(2-(N-methylcarbamoyl)-4-pyridyloxy)phenyl)urea.

In a particular embodiment, the pharmaceutically acceptable salt is tosylate, benzenesulfonate, hydrochloride, or methanesulfonate.

In another preferred embodiment, for the individual subject, the second therapeutic agent is administered 100-1000 mg per day, preferably 200-800 mg per day, and more preferably 400-800 mg per day.

In another preferred embodiment, for the individual subject, the second therapeutic agent is administered 1-3 times per day, and preferably the second therapeutic agent is administered twice per day.

In another preferred embodiment, for the individual subject, the dose of the immune effector cell per administration is about $1 \times 10^5 - 1 \times 10^8$ cells/kg subject weight, and more preferably the dose per administration is about $1 \times 10^5 - 1 \times 10^7$ cells/kg subject weight.

In another preferred embodiment, the immune effector cell and the second therapeutic agent are administered in no particular order; the second therapeutic agent may be administered first and then the immune effector cell; or they may be administered simultaneously; the immune effector cell may also be administered first and then the second therapeutic agent, and preferably the immune effector cell is administrated during the administration of the second therapeutic agent.

In a particular embodiment, the second therapeutic agent is administered orally.

In another preferred embodiment, the receptor is selected from: chimeric antigen receptor (CAR), T cell receptor (TCR), T cell fusion protein (TFP), T cell antigen coupler (TAC), or a combination thereof.

In a particular embodiment, the chimeric antigen receptor comprises:

(i) an antibody or a fragment thereof that specifically recognizes a tumor antigen, the transmembrane region of CD28 or CD8, the co-stimulatory signal domain of CD28, and the intracellular domain of CD3ζ; or (ii) an antibody or a fragment thereof that specifically recognizes a tumor antigen, the transmembrane region of CD28 or CD8, the co-stimulatory signal domain of CD137, and the intracellular domain of CD3ζ; or (iii) an antibody or a fragment thereof that specifically recognizes a tumor antigen, the transmembrane region of CD28 or CD8, the co-stimulatory signal domain of CD28, the co-stimulatory signal domain of CD137, and the intracellular domain of CD3ζ.

In a particular embodiment, the tumor antigen is selected from: thyroid stimulating hormone receptor (TSHR); CD171; CS-1; C-type lectin-like molecule-1; ganglioside GD3; Tn antigen; CD19; CD20; CD22; CD30; CD70; CD123; CD138; CD33; CD44; CD44v7/8; CD38; CD44v6; B7H3(CD276); B7H6; KIT(CD117); interleukin 13 receptor subunit α (IL-13Rα); interleukin 11 receptor α (IL-11Rα); prostate stem cell antigen (PSCA); prostate specific membrane antigen (PSMA); carcinoembryonic antigen (CEA); NY-ESO-1; HIV-1 Gag; MART-1; gp100; tyrosinase; mesothelin; EpCAM; protease serine 21 (PRSS21); vascular endothelial growth factor receptor; Lewis (Y) antigen; CD24; platelet derived growth factor receptor β (PDGFR-β); stage-specific embryonic antigen-4 (SSEA-4); cell surface-associated mucin 1 (MUC1); MUC6; epidermal growth factor receptor family and its mutants (EGFR, EGFR2, ERBB3, ERBB4, EGFRvIII); neural cell adhesion molecule (NCAM); carbonic anhydrase IX (CAIX); LMP2; ephrin A receptor 2 (EphA2); fucosyl GM1; sialyl Lewis adhesion molecule (sLe); ganglioside GM3 (aNeu5Ac(2-3)bDGalp(1-4)bDGlcp(1-1)Cer; TGS5; high molecular weight melanoma associated antigen (HMWMAA); o-acetyl GD2 ganglioside (OAcGD2); folate receptor; tumor vascular endothelial marker 1 (TEM1/CD248); tumor vascular endothelial marker 7 related (TEM7R); claudin 6, claudin 18.2, claudin 18.1; ASGPR1; CDH16; 5T4; 8H9; αvβ6 integrin; B cell maturation antigen (BCMA); CA9; kappa light chain; CSPG4; EGP2, EGP40; FAP; FAR; FBP; embryonic AchR; HLA-A1, HLA-A2; MAGEA1, MAGE3; KDR; MCSP; NKG2D ligand; PSC1; ROR1; Sp7; SURVIVIN; TAG72; TEM1; fibronectin; tenascin; carcinoembryonic variant of tumor necrosis zone; G protein-coupled receptor family C group 5 member D (GPRC5D); X chromosome open reading frame 61 (CXORF61); CD97; CD179a; anaplastic lymphoma kinase (ALK); polysialic acid; placenta-specific 1 (PLAC1); hexose part of globoH glycoceramide (GloboH); breast differentiation antigen (NY-BR-1); uroplakin 2 (UPK2); hepatitis A virus cell receptor 1 (HAVCRi); adrenaline receptor 3 (ADRB3); pannexin 3 (PANX3); G protein coupled receptor 20 (GPR20); lymphocyte antigen 6 complex locus K9 (LY6K); olfactory receptor 51E2 (OR51E2); TCRγ alternate reading frame protein (TARP); Wilms tumor protein (WT1); ETS translocation variant gene 6 (ETV6-AML); sperm protein 17 (SPA17); X antigen family member 1A (XAGE1); angiopoietin binding cell surface receptor 2 (Tie2); melanoma cancer testis antigen-1 (MAD-CT-1); melanoma cancer testis antigen-2 (MAD-CT-2); Fos-related antigen 1; p53 mutant; human telomerase reverse transcriptase (hTERT); sarcoma translocation breakpoint; melanoma inhibitor of apoptosis (ML-IAP); ERG (transmembrane protease serine 2 (TM-PRSS2) ETS fusion gene); N-acetylglucosamine transferase V (NA17); paired box protein Pax-3 (PAX3); androgen receptor; cyclin Bi; V-myc avian myelocytomatosis viral oncogene neuroblastoma-derived homolog (MYCN); Ras homolog family member C (RhoC); cytochrome P450 1B1 (CYP1B1); CCCTC binding factor (zinc finger protein)-like (BORIS); squamous cell carcinoma antigen 3 (SART3) recognized by T cells; paired box protein Pax-5 (PAX5); proacrosin binding protein sp32 (OYTES); lymphocyte specific protein tyrosine kinase (LCK); A-kinase anchoring protein 4 (AKAP-4); synovial sarcoma X breakpoint 2 (SSX2); CD79a; CD79b; CD72; leukocyte-associated immunoglobulin-like receptor 1 (LAIR1); Fc fragment of IgA receptor (FCAR); leukocyte immunoglobulin-like receptor subfamily member 2 (LILRA2); CD300 molecular-like family member f (CD300LF); C-type lectin domain family 12 member A (CLEC12A); bone marrow stromal cell antigen 2 (BST2); EGF-like module containing mucin-like hormone receptor-like 2 (EMR2); lymphocyte antigen 75 (LY75); glypican-3 (GPC3); Fc receptor-like 5 (FCRL5); immunoglobulin lambda-like polypeptide 1 (IGLL1).

In a particular embodiment, the tumor antigen is a solid tumor antigen. Preferably, the solid tumor antigen is vascular endothelial growth factor receptor, EGFR, EGFRvIII, GPC3, or claudin 18.2. More preferably, the solid tumor antigen is GPC3, EGFR, EGFRvIII, or vascular endothelial growth factor receptor.

In one embodiment, the vascular endothelial growth factor receptor is vascular endothelial growth factor receptor 2 (VEGFR2).

In a particular embodiment, the solid tumor antigen is GPC3.

In a particular embodiment, the antibody specifically recognizing a tumor antigen is an antibody targeting glypican-3 (GPC3).

In a preferred embodiment, the antibody specifically recognizing a tumor antigen comprises HCDR1, HCDR2, HCDR3 respectively represented by SEQ ID NOs: 15, 16, 17, and LCDR1, LCDR2, LCDR3 respectively represented by SEQ ID NOs: 18, 19, 20.

In a particular embodiment, the amino acid sequence of the antibody specifically recognizing the tumor antigen has at least 90% identity with the sequence of SEQ ID NO: 14.

In a particular embodiment, the amino acid sequence of the chimeric antigen receptor has at least 90% identity with the sequence of SEQ ID NO: 21, 22, 23 or 24.

In a preferred embodiment, the treatment is determined by the following clinical outcome or a combination thereof: increased, enhanced, or prolonged anti-tumor activity of the immune effector cell; increased number of anti-tumor immune effector cells or the activated immune effector cells as compared with the number before treatment.

In a particular embodiment, the clinical outcome is selected from: tumor regression; tumor shrinkage; tumor necrosis; anti-tumor response through the immune system; tumor expansion, recurrence or spread or a combination thereof.

In a particular embodiment, the therapeutic effect is predicted by: the presence of immune effector cells, or the presence of genetic markers indicative of T cell inflammation, or a combination thereof; preferably by detecting changes in the levels of IFN-γ and TNFα.

In a particular embodiment, the tumor comprises: blood cancer, breast cancer, glioma, colon cancer, rectal cancer, renal cell carcinoma, liver cancer, lung cancer, small intestine cancer, esophageal cancer, melanoma, bone cancer, pancreatic cancer, skin cancer, head and neck cancer, skin or intraocular malignant melanoma, uterine cancer, ovarian cancer, rectal cancer, anal cancer, stomach cancer, testicular cancer, uterine cancer, fallopian tube cancer, endometrial cancer, cervical cancer, vagina cancer, vulva cancer, Hodgkin's disease, non-Hodgkin's lymphoma, endocrine system cancer, thyroid cancer, parathyroid cancer, adrenal cancer, soft tissue sarcoma, urethral cancer, penile cancer, childhood solid tumor, bladder cancer, renal or ureteral cancer, renal pelvis cancer, central nervous system (CNS) tumor, primary CNS lymphoma, tumor angiogenesis, spinal tumor, brainstem glioma, pituitary adenoma, Kaposi's sarcoma, epidermoid carcinoma, squamous cell carcinoma, T-cell lymphoma, environmentally induced cancer, a combination of the cancers, and the metastatic foci of the cancer. Preferably, the tumor is selected from liver cancer, renal cell carcinoma, squamous cell lung carcinoma, and thyroid cancer.

In a particular embodiment, the immune effector cell include: T cell, B cell, natural killer cell (NK cell), natural killer T cell (NKT cell), mastocyte, or bone marrow-derived phagocyte, or a combination thereof; preferably, the immune effector cell is selected from autologous T cell, allogeneic T cell, or allogeneic NK cell; and more preferably, the T cell is an autologous T cell.

In the fourth aspect of the present invention, provided is use of an immune effector cell expressing a receptor that recognizes a tumor antigen in the preparation of a medicament, characterized in that the medicament is administrated in combination with sorafenib.

In a particular embodiment, the above application is used for treating a tumor in human patients, wherein the cell and sorafenib are formulated to provide a better or greater therapeutic effect obtained by using the cells and sorafenib alone, i.e., the cell and sorafenib are formulated to provide a greater therapeutic effect than when each of the reagents is used alone.

In the fifth aspect of the present invention, provided is a kit for treating a tumor, characterized in that the kit comprises:

1) an immune effector cell expressing a receptor that recognizes a tumor antigen;
2) sorafenib;
3) a container for containing the above substances of 1) and 2); and
4) instructions for using the kit to treat a tumor;

wherein the immune effector cell and sorafenib are formulated to provide a greater therapeutic effect than when each of the reagents is used alone; preferably, the immune effector cell is CAR T cell; and more preferably, the CAR T cell specifically recognizes EGFR, EGFRvIII, glypican-3, claudin 18.2, and BCMA.

In a particular embodiment, the CAR T cell specifically recognizes glypican-3.

In the sixth aspect of the present invention, provided is a product for treating a tumor, characterized in that the product comprises: an immune effector cell and a second therapeutic agent, and the immune effector cell expresses a receptor recognizing a tumor antigen.

The product includes:

1) an immune effector cell expressing a receptor that recognizes a tumor antigen;
2) sorafenib (a compound of formula II);
3) a container for containing the above substances of 1) and 2); and
4) instructions for using the product to treat a tumor;

wherein the immune effector cell express a chimeric antigen receptor that recognizes a tumor antigen, and the immune effector cell and the second therapeutic agent have the same definitions as mentioned above in the first, second, and third aspects of the present invention.

In the sixth aspect of the present invention, provided is use of an immune effector cell expressing a receptor that recognizes a tumor antigen and a second therapeutic agent in the preparation of a medicament or a product for treating a tumor in human patients, wherein the medicament formulated by the cell and the second therapeutic agent can provide a superior or greater therapeutic effect when the cell and the second therapeutic agent are each used alone.

The immune effector cell and the second therapeutic agent have the same definitions as mentioned above in the first, second, and third aspects of the present invention.

In a particular embodiment of the present invention, provided is a method for treating a tumor or reducing the growth, survival or viability of cancer cells, characterized in that an immune effector cell and sorafenib are administered to an individual suffering from a tumor, wherein the immune effector cell expresses a chimeric antigen receptor recognizing a tumor antigen. The chimeric antigen receptor has an antibody or a fragment thereof that specifically recognizes a tumor antigen, a transmembrane domain, and a cytoplasmic signaling domain. Wherein the antibody or a fragment thereof that specifically recognizes a tumor antigen comprises HCDR1, HCDR2, HCDR3 respectively represented by SEQ ID NOs: 15, 16, 17, and LCDR1, LCDR2, LCDR3 respectively represented by SEQ ID NOs: 18, 19, 20. Wherein, the tumor is liver cancer, and the cancer cells are liver cancer cells.

In a particular embodiment of the present invention, provided is a method for treating a tumor or reducing the growth, survival or viability of cancer cells, characterized in that an immune effector cell and regorafenib are administered to an individual suffering from a tumor, wherein the immune effector cell expresses a chimeric antigen receptor recognizing a tumor antigen. The chimeric antigen receptor has an antibody or a fragment thereof that specifically recognizes a tumor antigen, a transmembrane domain, and a cytoplasmic signaling domain. Wherein the antibody or a fragment thereof that specifically recognizes a tumor antigen comprises HCDR1, HCDR2, HCDR3 respectively represented by SEQ ID NOs: 15, 16, 17, and LCDR1, LCDR2, LCDR3 respectively represented by SEQ ID NOs: 18, 19, 20. Wherein, the tumor is liver cancer, and the cancer cells are liver cancer cells.

In a particular embodiment of the present invention, provided is a product or kit for treating a tumor, characterized in that the product or kit comprises:
1) an immune effector cell;
2) sorafenib or regorafenib;
3) a container for containing the above substances of 1) and 2); and
4) instructions for using the product to treat a tumor;

wherein the immune effector cell expresses a chimeric antigen receptor recognizing a tumor antigen. The chimeric antigen receptor has an antibody or a fragment thereof that specifically recognizes a tumor antigen, a transmembrane domain, and a cytoplasmic signaling domain. Wherein the antibody or a fragment thereof that specifically recognizes a tumor antigen comprises HCDR1, HCDR2, HCDR3 respectively represented by SEQ ID NOs: 15, 16, 17, and LCDR1, LCDR2, LCDR3 respectively represented by SEQ ID NOs: 18, 19, 20. Wherein, the tumor is liver cancer, and the cancer cells are liver cancer cells.

It should be understood that, within the scope of the present invention, the above-mentioned technical features of the present invention and the technical features specifically described in the following (e.g., in the Examples) may be combined with each other to form a new or preferred technical solution. Due to space limitations, they will not be repeated here one by one.

The beneficial effects of the present invention:
1. Using the compound of formula I provided by the present invention in combination with the immune effector cell may significantly improve the ability to kill tumor cells.
2. Adopting the therapeutic protocols of the present invention may fight against the immunosuppression in the cancer microenvironment, thereby significantly enhancing the effect on solid tumors, and also having better effect on refractory and progressive cancers.

DETAILED DESCRIPTION OF EMBODIMENTS

Figure 1A:
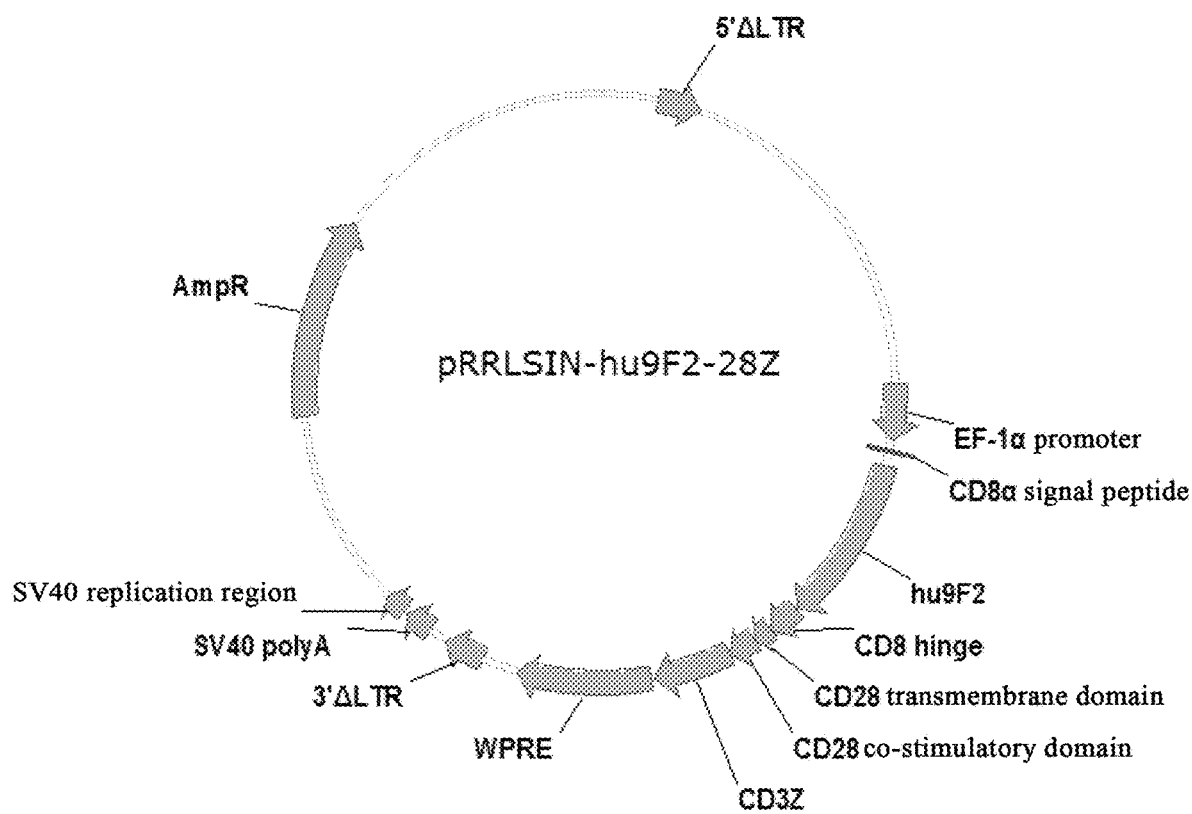
FIG. 1A is the plasmid profile of PRRLSIN-hu9F2-28Z.

The present invention relates to the combination of an immune effector cell and a second therapeutic agent (a compound of formula I) in the treatment of a tumor. It should be understood that, the present invention is not limited to the methods and experimental conditions described. Unless specifically defined, all technical and scientific terms used herein have the same meaning as commonly understood by those skilled in the fields of gene therapy, biochemistry, genetics, molecular biology, and medicinal chemistry.

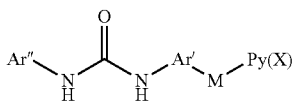

Methods and materials similar or equivalent to those described herein may be used in the practice or testing of the present invention. All publications, patent applications, patents and other references mentioned in this application are incorporated herein by reference in their entirety. In case of conflict, the specification, including definitions, shall prevail. In addition, unless otherwise specified, the materials, methods, and examples are merely illustrative and not to be construed as limiting.

Unless otherwise specified, the practice of the present invention will use traditional techniques of cell biology, cell culture, molecular biology, transgenic biology, microbiology, recombinant DNA and immunology, which all fall within the technical scope of the art. These techniques are fully explained in the literatures. See, for example, Current Protocols in Molecular Biology (Frederick M.AUSUBEL, 2000, Wiley and Sons Inc., Library of Congress, USA); Molecular Cloning: A Laboratory Manual, Third Edition, (Sambrook et al., 2001, Cold Spring Harbor, New York: Cold Spring Harbor Laboratory Press); Oligonucleotide Synthesis (M. J. Gaited, 1984); Mullis et al. U.S. Pat. No. 4,683,195; Nucleic Acid Hybridization (B. D. Harries & S. J. Higginseds. 1984); Transcription And Translation (B. D. Hames & S. J. Higginseds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), especially Vols. 154 and 155 (Wuetal. eds.) and Vol. 185, "Gene Expression Technology" (D. Goeddel, ed.); Gene Transfer Vectors For Mammalian Cells (J. H. Miller and M. P. Caloseds., 1987, Cold Spring Harbor Laboratory); Immunochemical Methods In Cell And Molecular Biology (Mayer and Walker, eds., Academic Press, London, 1987); Hand book Of Experimental Immunology, Volumes I-IV (D. M. Weir and C. C. Blackwell, eds., 1986); and Manipulating the Mouse Embryo (Cold Spring Harbor Laboratory Press, Cold Spring Harbor, N.Y., 1986).

The present invention is derived at least in part from the recognition that: adopting one or more cycles and/or doses of a combination treatment regimen in which the second therapeutic agent and an immune effector cell are administered continuously, in any order, or substantially simultaneously for treating cancers in some subjects, the activity and/or number of the immune cells may be more effectively increased, enhanced or prolonged, thereby achieving anti-tumor effect.

The term "about" used herein, refers to the usual error range of each value easily known to those skilled in the art. When "about" is used herein before a value or parameter, it includes (and describes) an embodiment referring to the value or parameter itself. For example, description of "about X" includes description of "X". For example, "about" or "including" may mean the standard deviation within 1 or more than 1 according to the actual practical in the field. Or "about" or "comprising" can mean a range of up to 10% (i.e., ±10%). For example, about 5 mg can include any number between 4.5 mg and 5.5 mg. When a specific value or composition is provided in the application and the scope of the patent application, unless otherwise indicated, "about" or "including" shall be assumed to be within the acceptable error range of the specific value or composition.

Any concentration range, percentage range, ratio range, or integer range described herein should be understood to include any integer within the stated range, and where appropriate, a value of its fraction (for example, one-tenth and one-hundredth of an integer), unless otherwise indicated.

The "dose" mentioned herein, may be expressed as a dose calculated on the basis of weight or a dose calculated on the basis of body surface area (BSA). The dose calculated on the basis of weight is the dose to be administered to the patient calculated on the basis of the weight of the patient, for example, mg/kg. The dose calculated on the basis of BSA is the dose to be administered to the patient calculated based on the basis of the surface area of the patient, for example, mg/m2.

In a particular embodiment, the second therapeutic agent used in the present invention is a compound of formula I, or a pharmaceutically acceptable salt thereof.

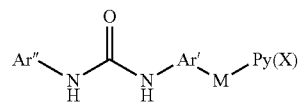

wherein Ar' is an unsubstituted or substituted phenyl, and the substituent is selected from halogen and C1-10 alkyl, M is one or more bridging groups selected from —O— or —S—, Py(X) is X-substituted pyridyl, X is —C(O)$R_x$, wherein $R_x$ is $NR_aR_b$, and each of $R_a$ and $R_b$ is selected from:
  a) hydrogen,
  b) C1-10 alkyl,
  c) C1-10 alkyl substituted by hydroxy,
  d) C3-12 cycloalkyl containing 1-3 N, S or O heteroatoms, and
  e) —OSi($R_f$)3, wherein Reis C1-10 alkyl, Ar" is unsubstituted or substituted phenyl, and the substituent is selected from halogen or Wn, wherein n=0-3, and W is selected from:
  a) C1-10 alkyl,
  b) C1-10 alkoxy,
  c) C1-10 haloalkyl, and
  d) C3-12 heteroaryl containing 1-3 N, S or O heteroatoms, and the heteroaryl may be substituted by C1-10 alkyl.

In the present invention, the term "C1-10 alkyl" refers to any linear or branched chain group containing 1-10 carbon atoms, such as methyl, ethyl, n-propyl, isopropyl, n-butyl, isobutyl, tert-butyl, sec-butyl, n-pentyl, tert-pentyl, n-hexyl, n-heptyl, n-octyl, isooctyl, 2-ethylhexyl, n-nonyl, isononyl, n-decyl, etc.

The term "C1-10 alkoxy" refers to any of the above mentioned C1-C10 alkyl which is connected to the rest of the molecule through an oxygen atom (—O—).

The term "halogen" refers to fluorine, chlorine, bromine, and iodine.

The term "haloalkyl" refers to fluoroalkyl, chloroalkyl, bromoalkyl, and iodoalkyl.

The term "C3-12 cycloalkyl" refers to a non-aromatic, saturated or unsaturated, monocyclic or bicyclic hydrocarbon ring having 3-12 carbon atoms. Exemplary "cycloalkyl" includes, but is not limited to, cyclopropyl, cyclobutyl, cyclopentyl, cyclohexyl, cycloheptyl, and the like.

The term "heteroaryl" refers to an aromatic heterocyclic ring, usually a 5- to 8-membered heterocyclic ring having 1-3 heteroatoms selected from N, O or S; the heteroaryl ring may optionally be further fused or connected to aromatic and non-aromatic carbocyclic and heterocyclic rings. Non-limiting examples of the heteroaryl are, for example, pyridyl, pyrazinyl, pyrimidinyl, pyridazinyl, indolyl, imidazolyl, thiazolyl, isothiazolyl, thiaoxazolyl, pyrrolyl, phenylpyrrolyl, furanyl, phenyl-furanyl, oxazolyl, isoxazolyl, pyrazolyl, thienyl, benzothienyl, isoindolinyl, benzimidazolyl, indazolyl, quinolyl, isoquinolyl, 1,2,3-triazolyl, 1-phenyl-1,2,3-triazolyl, 2,3-indolinyl, 2,3-dihydrobenzofuranyl, 2,3-dihydrobenzothienyl, benzopyranyl, 2,3-dihydrobenzoxazinyl, 2,3-dihydroquinoxalinyl, etc.

From all the above descriptions, it is obvious to those skilled in the art that any group whose name is a compound name, such as "arylamino", shall refer to it is conventionally constructed from the moiety derived therefrom, such as from an aryl substituted amino group, wherein the aryl is as defined above.

In a particular embodiment, the compounds of formula I include, but are not limited to, the compounds of formula II and formula III.

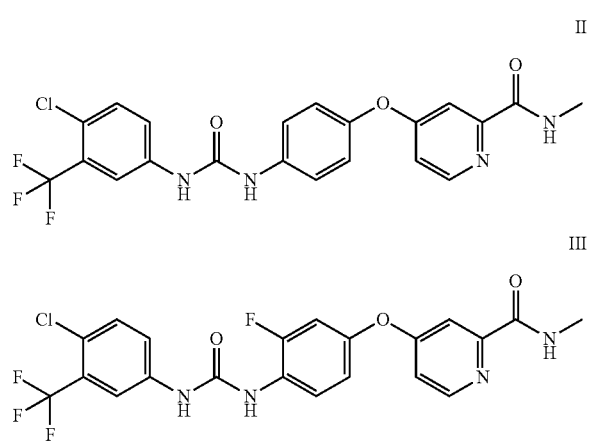

In a particular embodiment, the second therapeutic agent may be a pharmaceutically acceptable salt of the compound of formula II, such as tosylate, benzenesulfonate, hydrochloride, methanesulfonate and the like.

In a particular embodiment, a hydrate, such as monohydrate, dehydrate of the compound of formula III may be used; and its pharmaceutically acceptable salt, such as hydrochloride, etc. may also be used.

The applicant found that, the second therapeutic agent such as Compound II may not only promote CAR T cells to secrete the cytokine IL2, but also promote the infiltration of CAR T cells into tumor tissues, and improve the anti-tumor effect. Therefore, the combination therapy of a second therapeutic agent such as compound II and an immune cell targeting tumor-specific antigens may significantly improve the anti-tumor effect.

The applicant also found that, the present invention can not only improve the anti-cancer effect on refractory cancers, but also can achieve a good anti-tumor effect even if lymphocyte clearance is not performed when using CAR-T cells, thereby greatly alleviating the low effect of the anti-cancer therapy caused by lymphocyte clearance, and reducing the toxic side effect caused by damage to normal tissues, especially the severe suppression of bone marrow.

In a particular embodiment, the second therapeutic agent such as compound II may be safely administered as itself orally or non-orally, or safely administered as a composition formed with a pharmaceutically acceptable carrier, excipient and other additives (such as tablets, sustained release preparations, capsules, injections, solutions) orally or non-orally. When administered orally, the composition may be formulated into tablets, dragees or capsules. To prepare an oral composition, lactose or starch may be used as a carrier; and gelatin, sodium carboxymethylcellulose, methylcellulose polyvinylpyrrolidone, etc. are suitable binding agents or granulating agents. As a disintegrant, starch or microcrystalline cellulose may be selected; and talc, colloidal silica, glyceryl stearate, calcium or magnesium stearate, etc. are often used as suitable anti-adhesion agents and lubricants. For example, tablets may be prepared by compressing wet granules. The active ingredient and the carrier, and an optional disintegration additive form a mixture; the mixture and aqueous solution, alcoholic or aqueous alcoholic solution of a binder are granulated in a suitable equipment, and then a mixture of the dried granules and the added other disintegration agent, lubricant and anti-adhesive agent is pressed into tablets. In order to increase the solubility, the heterocyclic derivatives may be freed to prepared into pharmaceutically acceptable organic acids, preferably methanesulfonic acid, fumaric acid, etc., so as to facilitate administration in the form of injections, although the dosage is changed depending on the subject, manner of administration, symptoms and other factors.

In a particular embodiment, the second therapeutic agent is sorafenib (having the structure shown by the compound of formula II), preferably, sorafenib tosylate.

In a particular embodiment, the second therapeutic agent is ragorafenib (having the structure shown by the compound of formula III), preferably, sorafenib tosylate.

The applicant found that, due to the synergistic effect of sorafenib and CAR-T cells, even a low dose of sorafenib can achieve better effect, so the technical solution of the present invention can reduce the toxic side effect of sorafenib.

In a particular embodiment, the low-dose second therapeutic agent refers to a dose lower than the dose that can achieve clinical therapeutic effect when used alone. For example, low-dose sorafenib refers to a dose lower than the dose of sorafenib that can achieve clinical therapeutic effect when used alone, particularly it refers to the clinically recommended dose of sorafenib: the recommended dose of sorafenib is 0.4 g (2×0.2 g) each time, twice per day; or it is lower than the approximate concentration 6.5 uM in the patient's body after compound II is administrated alone in the clinical trial.

The dosage of sorafenib in the present invention may be lower than the clinical effective dosage. In some embodiments, the average concentration of sorafenib in the body of an individual with a tumor is about 6, 5.5, 5, 4.5, 4, 3.5, 3, 2.5, 2, 1.5, 1, 0.95, 0.9, 0.85, 0.8, 0.75, 0.7, 0.65, 0.6, 0.55, 0.5, 0.45, 0.4, 0.35, 0.3, 0.25, 0.2, 0.15, 0.1, 0.095, 0.09, 0.085, 0.08, 0.075, 0.07, 0.065, 0.06, 0.055, 0.05, 0.045, 0.04, 0.035, 0.034, 0.033, 0.032, 0.031, 0.03, 0.029, 0.028, 0.027, 0.026, 0.025, 0.024, 0.023, 0.022, 0.021, 0.02, 0.019, 0.018, 0.017, 0.016, 0.015, 0.014, 0.013, 0.012, 0.011, 0.01, 0.009, 0.008, 0.007, 0.006, 0.005, 0.004, 0.003, 0.002, or 0.001 uM. In some embodiments, the daily oral dose of sorafenib for an individual with a tumor is about 700, 650, 600, 550, 500, 450, 400, 350, 300, 290, 280, 270, 260, 250, 240, 230, 220, 210, 200, 190, 180, 170, 160, 150, 140, 130, 120, 110, 100, 90, 80, 70, 60, 50, 40, 30, 20, 10, 9, 8, 7, 6, 5, 4, 3, 2 or 1 mg, preferably 400-800 mg/day.

Sorafenib may be administered once per day, or multiple times per day, such as twice per day.

In the case of sorafenib, the daily dosage may be 100-1000 mg, preferably 200-800 mg is administered per day, and more preferably 400-800 mg is administered per day.

In the present invention, the immune effector cell and the second therapeutic agent are administered in no particular order; the second therapeutic agent may be administered first and then the immune effector cell; they may also be administered simultaneously; the immune effector cell may also be administered first and then the second therapeutic agent.

In some embodiments, the immune effector cell is administrated 1 hour, 2 hours, 3 hours, 4 hours, 5 hours, 6 hours, 7 hours, 8 hours, 9 hours, 10 hours, 11 hours, 12 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 1 month prior to the second therapeutic agent, or any combination thereof.

In some embodiments, the immune effector cell is administrated 1 hour, 2 hours, 3 hours, 4 hours, 5 hours, 6 hours, 7 hours, 8 hours, 9 hours, 10 hours, 11 hours, 12 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 1 month after the second therapeutic agent, or any combination thereof.

In some embodiments, the second therapeutic agent is continuously administered until the doctor evaluates that the drug needs to be stopped or the drug may be stopped, e.g., the drug is stopped to administrate after the doctor evaluates that the disease is completely alleviated or progressed. In some embodiments, the second therapeutic agent is continuously administered for 1 month, 2 months, 3 months, 4 months, 5 months, 6 months, 7 months, 8 months, 9 months, 10 months, 11 months, 12 months, or even longer. The immune effector cell is administered during the continuous administration of the second therapeutic agent.

The term "immune effector cell" refers to a cell that participates in an immune response, for example, promotes an immune effect. Examples of immune effector cell includes T cell, for example, α/β T cell and γ/δ T cell, B cell, natural killer (NK) cell, natural killer T (NKT) cell, mast cell, and bone marrow-derived phagocyte. Preferably, the T cell includes autologous T cell, xenogeneic T cell, and allogeneic T cell; and the natural killer cell is allogeneic NK cell. As used herein, the term "immune effector function, or immune effector response" refers to, for example, a function or response of an immune effector cell that enhances or promotes an immune attack of a target cell. For example, immune effector function or response refers to the property of T cell or NK cell that promotes the killing of target cells or inhibits the growth or proliferation.

The terms "therapeutically effective amount", "therapeutically effective", and "effective amount" are used interchangeably herein, and refer to the amount of a compound, preparation, substance, or composition that is effective to achieve a specific biological result as described herein, such as, but not limited to, an amount or dose sufficient to promote T cell response. When referring to "immunologically effective amount", "anti-tumor effective amount", "tumor-inhibiting effective amount" or "therapeutically effective amount", the exact amount of the immune effector cell and therapeutic agent according to the present invention to be administered, may be determined by a physician in consideration of the individual's age, weight, tumor size, degree of infection or metastasis, and the condition of the patient (subject). An effective amount of an immune effector cell refers to, but is not limited to, the number of the immune effector cells capable of increasing, enhancing or prolonging the anti-tumor activity of the immune effector cell; increase of the number of anti-tumor immune effector cells or activated immune effector cells; the number of the immune effector cells capable of promoting the secretion of IFN-γ and TNFα, tumor regression, tumor shrinkage and tumor necrosis.

The term "no lymphocyte clearance" or "not subjected to lymphocyte clearance" means that the lymphocytes in the subject are not eliminated, including but not limited to: not administrating a lymphocyte scavenger, not conducting systemic radiation therapy, or a combination thereof, or other means to cause clearance of lymphocyte number. However, after administrating a lymphocyte scavenger, conducting systemic radiation therapy, or a combination thereof, or other means that cause clearance of lymphocyte number, when the lymphocyte clearance rate in the subject is less than 60%, for example, the lymphocyte clearance rate in the body is 55%, 50%, 45%, 40%, 35%, 30%, 25%, 20%, 15% or 10%, it will also fall into the scope of "no lymphocyte clearance" as the equivalent in this application.

In this application, the lymphocyte clearance rate may be calculated by detecting the number of lymphocytes before lymphocyte clearance and detecting the number of lymphocytes after lymphocyte clearance, for example, the number of lymphocytes before administrating a drug for lymphocyte clearance minus the number of lymphocytes after administrating a drug for lymphocyte/the number of lymphocytes before administrating a drug for lymphocyte clearance. The detection of lymphocytes may be performed by a method for detecting the lymphocyte number commonly used by medical personnel, such as blood routine examination.

The terms "peptide", "polypeptide" and "protein" are used interchangeably, and refer to a compound formed from amino acid residues covalently linked by peptide bonds. A protein or peptide needs to contain at least two amino acids, and there is no limit to the maximum number of amino acids that may be included in the sequence of a protein or peptide. A polypeptide includes any peptide or protein containing two or more amino acids bonded to each other by peptide bonds. The "chimeric receptor" as used herein refers to a fusion molecule formed by linking DNA fragments or corresponding cDNAs of proteins from different sources through gene recombination technology, including extracellular domain, transmembrane domain and intracellular domain. Chimeric receptors include, but are not limited to: chimeric antigen receptor (CAR), modified T cell (antigen) receptor (TCR), T cell fusion protein (TFP), and T cell antigen coupler (TAC).

As used herein, "chimeric antigen receptor" or "CAR" refers to a set of polypeptides that, when in an immune effector cell, provide said cell with specificity for target cells (usually cancer cells) and may generate intracellular signal. CAR usually comprises at least one extracellular antigen binding domain, transmembrane domain and cytoplasmic signaling domain (also referred to herein as "intracellular signaling domain"), which includes the functional signaling domain derived from stimulatory molecules and/or co-stimulatory molecules as defined below. In certain aspects, a set of polypeptides are adjacent to each other. The set of polypeptides includes a dimerization switch enabling the polypeptides to couple with each other when a dimerization molecule is present, for example, an antigen binding domain may be enabled to couple to an intracellular signaling domain. In one aspect, the stimulatory molecule is a ((zeta) chain binding to the T cell receptor complex. In one aspect, the cytoplasmic signaling domain further comprises one or more functional signaling domains derived from at least one co-stimulatory molecule as defined below. In one aspect, the co-stimulatory molecule is selected from the co-stimulatory molecules described herein, e.g., 4-1BB (i.e., CD137), CD27, and/or CD28. In one aspect, the CAR comprises a chimeric fusion protein comprising an extracellular antigen binding domain, a transmembrane domain, and an intracellular signaling domain, wherein the intracellular signaling domain comprises a functional signaling domain derived from a stimulatory molecule. In one aspect, the CAR comprises a chimeric fusion protein comprising an extracellular antigen binding domain, a transmembrane domain, and an intracellular signaling domain, wherein the intracellular signaling domain comprises a functional signaling domain derived from a co-stimulatory molecule and a functional signaling domain derived from a stimulatory molecule. In one aspect, the CAR comprises a chimeric fusion protein comprising an extracellular antigen binding domain, a transmembrane domain, and two functional signaling domains derived from one or more co-stimulatory molecules.

In one aspect, the present invention contemplates the modification of the amino acid sequence of the starting antibody or fragment thereof (e.g., scFv) that produces a functionally equivalent molecule. For example, the VH or VL of the antigen-binding domain of the cancer-associated antigen described herein, such as scFv included in the CAR, may be modified to retain at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity of the initial VH or VL framework (e.g., scFv) of the antigen-binding domain of the cancer-associated antigen described herein. The present invention contemplates the modification of the entire CAR construct, e.g., the modification of one or more amino acid sequences of multiple domains of the CAR construct, so as to produce a functionally equivalent molecule. The CAR construct may be modified to retain at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity of the starting CAR construct.

As used herein, the "transmembrane domain" may comprise one or more additional amino acids adjacent to the transmembrane region, for example, one or more amino acids associated with the extracellular region of the protein from which the transmembrane domain is derived (e.g., 1, 2, 3, 4, 5, 6, 7, 8, 9, 10 up to 15 amino acids in the extracellular region), and/or one or more additional amino acids associated with the extracellular region of the protein from which the transmembrane protein is derived (e.g., 1, 2, 3, 4, 5, 6, 7, 8, 9, 10 up to 15 amino acids in the intracellular region). In one aspect, the transmembrane domain is a domain related to one of the other domains of the chimeric receptor, for example, in one embodiment, the transmembrane domain may be from the same protein from which a signaling domain, a co-stimulatory domain or hinge domain is derived. In certain cases, a transmembrane domain may be selected, or modified by amino acid substitutions to prevent such a domain from binding to a transmembrane domain of the same or different surface membrane protein, for example, to minimize its interaction with other members of the receptor complex. In one aspect, the transmembrane domain is capable of undergoing homodimerization with another chimeric receptor on the cell surface of the cell expressing the chimeric receptor. In a different aspect, the amino acid sequence of the transmembrane domain may be modified or substituted, in order to minimize its interaction with the binding domain of the natural binding partner present in a cell expressing the same chimeric receptor. The transmembrane domain may be derived from natural or recombinant sources. When the source is natural, the domain may be derived from any membrane-binding protein or transmembrane protein. In one aspect, as long as the chimeric receptor binds to the target antigen, the transmembrane domain can transmit signal to the intracellular domain. The transmembrane domain specifically used in the present invention may include at least the following transmembrane domains: for example, α, β or ζ chains of T-cell receptors, CD28, CD27, CD3F, CD45, CD4, CD5, CD8, CD9, CD16, CD22, CD33, CD37, CD64, CD80, CD86, CD134, CD137, CD154. In certain embodiments, the transmembrane domain may include at least the following transmembrane regions: for example, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), NKp44, NKp30, NKp46, CD160, CD19, IL2Rβ, IL2Rγ, IL7Rα, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM, CRTAM, Ly9 (CD229), CD160 (BY55), PSGL1, CD100 (SEMA4D), SLAMF6 (NTB-A, Ly108), SLAM (SLAMFI, CD150, IPO-3), BLAME (SLAMF8), SELPLG (CD162), LTBR, PAG/Cbp, NKG2D, NKG2C.

In certain cases, the transmembrane domain may be connected to the extracellular region of the CAR via a hinge (e.g., a hinge from a human protein), for example, the antigen binding domain of the CAR. For example, in one embodiment, the hinge may be a human Ig (immunoglobulin) hinge (e.g., IgG4 hinge, IgD hinge), GS linker (e.g., GS linker described herein), KIR2DS2 hinge, or CD8a hinge. In one aspect, the transmembrane domain may be a recombinant one, and in this case it will mainly contain hydrophobic residues such as leucine and valine. In one aspect, a triplet of phenylalanine, tryptophan and valine may be found at each end of the recombinant transmembrane domain. Optionally, short oligopeptide or polypeptide linkers between 2 and 10 amino acids in length can form a bond between the transmembrane domain of the CAR and the cytoplasmic region. The glycine-serine dimer provides a particularly suitable linker.

As used herein, "cytoplasmic domain" includes intracellular signaling domain. The intracellular signaling domain is generally responsible for the activation of at least one of the normal effector functions of an immune cell into which the chimeric receptor has been introduced. The term "effector function" refers to the specialized function of a cell. The effector function of a T cell may be, for example, cytolytic activity or auxiliary activity, including secretion of cytokines. Therefore, the term "intracellular signaling domain" refers to a part of a protein that transduces effector function signal and guides a cell to perform specific function. Although the entire intracellular signaling domain can usually be used, in many cases it is not necessary to use the entire chain. In the case of using a truncated part of the intracellular signaling domain, such a truncated part may be used instead of the complete chain as long as it transduces effector function signal. Therefore, the term "intracellular signaling domain" means to include a truncated part of the intracellular signaling domain sufficient to transduce effector function signal.

It is well known that the signal generated by TCR alone is not sufficient to fully activate a T cell, and secondary and/or co-stimulatory signals are also required. Therefore, T cell activation may be called to be mediated by two different kinds of cytoplasmic signaling sequences: those that trigger antigen-dependent primary activation through TCR (primary intracellular signaling domains), and those that function in an antigen-independent manner so as to provide secondary or co-stimulatory signals (secondary cytoplasmic domains, e.g., co-stimulatory domains).

The term "stimulation" refers to the initial response induced by the binding of a stimulating molecule (e.g., TCR/CD3 complex or CAR) to its cognate ligand (or a tumor antigen in the case of CAR), and thereby mediating a signal transduction event (e.g., but it is not limited to, signal transduction via the TCR/CD3 complex, or signal transduction via a suitable NK receptor or the signaling domain of CAR). Stimulation may mediate the altered expression of certain molecules.

The term "stimulatory molecule" refers to a molecule expressed by an immune cell (e.g., T cell, NK cell, B cell) that provides a cytoplasmic signaling sequence, wherein the signaling sequence modulates the activation of an immune cell for at least some aspects of the signal transduction pathway of immune cells in a stimulating manner. In one aspect, the signal is a primary signal initiated by, for example, the binding of a TCR/CD3 complex to a peptide-loaded MHC molecule, and it leads to mediation of T cell responses, including, but not limited to, proliferation, activation, differentiation, and the like. The primary cytoplasmic signaling sequence that acts in a stimulating manner (also referred to as "primary signaling domain"), may contain what is called an immune receptor tyrosine-based activation motif or ITAM-based signaling motif. Particularly, examples of ITAM-containing cytoplasmic signaling sequences used in the present invention include, but are not limited to, those derived from: CD3ζ, common FcRγ (FCER1G), FcγRIIa, FcRβ (FcEpsilon R1b), CD3γ, CD3δ, CD3ε, CD79a, CD79b, DAP10 and DAP12. In a specific CAR of the present invention, the intracellular signaling domain in any one or more CARs of the present invention includes an intracellular signaling sequence, e.g., a primary signaling sequence of CD3-ζ. In a specific CAR of the present invention, the primary signaling sequence of CD3-ζ is the equivalent residues from human or non-human species such as mouse, rodent, monkey, ape and the like.

The term "co-stimulatory molecule" refers to a homologous binding partner on a T cell, which specifically binds a co-stimulatory ligand, thereby mediating the co-stimulatory response of a T cell, e.g., but not limited to, proliferation. A co-stimulatory molecule is a cell surface molecule other than an antigen receptor or the ligand thereof, and promotes effective immune response. Co-stimulatory molecules include, but are not limited to: MHC class I molecules, BTLA and Toll ligand receptors, and OX40, CD27, CD28, CDS, ICAM-1, LFA-1 (CD11a/CD18), ICOS (CD278) and 4-1BB (CD137). Further examples of such co-stimulatory molecules include CDS, ICAM-1, GITR, BAFFR, HVEM (LIGHTR), SLAMF7, NKp80 (KLRF1), NKp44, NKp30, NKp46, CD160, CD19, CD4, CD8a, CD80, IL2Rβ, IL2Rγ, IL7Rα, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1 CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAMI, CRTAM, Ly9 (CD229), CD160 (BY55), PSGL1, CD100 (SEMA4D), CD69, SLAMF6 (NTB-A, Ly108), SLAM (SLAMFI, CD150, IPO-3), BLAME (SLAMF8), SELPLG (CD162), LTBR, LAT, GADS, SLP-76, PAG/Cbp, CD19a, and a ligand that specifically binds to CD83.

The co-stimulatory intracellular signaling domain may be the intracellular part of a co-stimulatory molecule. Co-stimulatory molecules may be represented by the following protein families: TNF receptor protein, immunoglobulin-like protein, cytokine receptor, integrin, signaling lymphocyte activation molecule (SLAM protein), and NK cell receptor. Examples of such molecules include: CD27, CD28, 4-1BB (CD137), OX40, GITR, CD30, CD40, ICOS, BAFFR, HVEM, ICAM-1, antigen-1 (LFA-1) associated with lymphocyte function, CD2, CDS, CD7, CD287, LIGHT, NKG2C, NKG2D, SLAMF7, NKp80, NKp30, NKp44, NKp46, CD160, B7-H3, and a ligand that specifically binds to CD83, etc.

The intracellular signaling domain may include all the intracellular part or all the natural intracellular signaling domain of a molecule, or a functional fragment or a derivative thereof.

The term "4-1BB" refers to a member of the TNFR superfamily with the amino acid sequence provided in GenBank Accession No. AAA62478.2, or equivalent residues from non-human species such as mouse, rodent, monkeys, ape, etc.; and "4-1BB co-stimulatory domain" is defined as the amino acid residues 214-255 of GenBank Accession No. AAA62478.2, or equivalent residues from non-human species such as mouse, rodent, monkey, ape, etc. In one aspect, the "4-1BB co-stimulatory domain" is equivalent residues from human or from non-human species such as mouse, rodent, monkey, ape, and the like.

The term "scFv" refers to a fusion protein comprising at least one variable region antibody fragment including a light chain and at least one antibody fragment including a variable region of a heavy chain, wherein the light chain and heavy chain variable regions are contiguous (e.g., via a synthetic linker such as a short flexible polypeptide linker), and may be expressed as a single-chain polypeptide, and wherein the scFv retains the specificity of the intact antibody from which it is derived. Unless specified, as used herein, scFv may have the VL and VH variable regions in any order (for example, relative to the N-terminus and C-terminus of the polypeptide), i.e., the scFv may include VL-linker-VH or may include VH-linker-VL.

The term "antibody heavy chain" refers to the larger of the two polypeptide chains present in the antibody molecule in its naturally occurring configuration and it usually determines the type of antibody.

The term "antibody light chain" refers to the smaller of the two polypeptide chains present in an antibody molecule in its naturally occurring configuration. κ (k) and λ (l) light chains refer to the two main isotypes of antibody light chains.

The term "recombinant antibody" refers to an antibody produced by recombinant DNA technology, such as, for example, an antibody expressed by a phage or yeast expression system. The term should also be interpreted as referring to an antibody that has been produced by synthesizing a DNA molecule encoding the antibody (and wherein the DNA molecule expresses the antibody protein) or the amino acid sequence of the specified antibody, wherein the DNA or amino acid sequence has been obtained by recombinant DNA technology or amino acid sequence technology available and well-known in the art.

The term "antigen" or "Ag" refers to a molecule that causes an immune response. The immune response may involve the production of an antibody or the activation of a cell with specific immunity. Those skilled in the art should understand that virtually any macromolecule of all proteins or peptides may serve as an antigen. In addition, the antigen may be derived from recombinant or genomic DNA. When the term is used herein, those skilled in the art should understand it includes any DNA comprising a nucleotide sequence or part of a nucleotide sequence that encodes a protein causing an immune response. In addition, those skilled in the art should understand that the antigen need not be encoded only by the full-length nucleotide sequence of the gene. The present invention includes, but is not limited to, the use of partial nucleotide sequences with more than one gene, and these nucleotide sequences are arranged in different combinations to encode polypeptides that elicit a desired immune response. Moreover, those skilled in the art should understand that an antigen needs not be encoded by a "gene" at all. An antigen may be produced synthetically, or it may be derived from a biological sample, or it may be a macromolecule other than polypeptide. Such biological samples may include, but are not limited to, tissue samples, tumor samples, cells or fluids with other biological components.

"Tumor antigen" refers to a new substance or overexpressed product expressed in the canceration process of a cell. In certain aspects, the antigens of the hyperproliferative disorder according to the invention are derived from cancer. The tumor antigens of the present invention include, but are not limited to: thyroid stimulating hormone receptor (TSHR); CD171; CS-1; C-type lectin-like molecule-1; ganglioside GD3; Tn antigen; CD19; CD20; CD22; CD30; CD70; CD123; CD138; CD33; CD44; CD44v7/8; CD38; CD44v6; B7H3(CD276), B7H6; KIT(CD117); interleukin 13 receptor subunit α (IL-13Rα); interleukin 11 receptor α (IL-11Rα); prostate stem cell antigen (PSCA); prostate specific membrane antigen (PSMA); carcinoembryonic antigen (CEA); NY-ESO-1; HIV-1 Gag; MART-1; gp100; tyrosinase; mesothelin; EpCAM; protease serine 21 (PRSS21); vascular endothelial growth factor receptor, vascular endothelial growth factor receptor 2 (VEGFR2); Lewis (Y) antigen; CD24; platelet-derived growth factor receptor β (PDGFR-β); stage-specific embryonic antigen-4 (SSEA-4); cell surface-associated mucin 1 (MUC1), MUC6; epidermal growth factor receptor family and its mutants (EGFR, EGFR2, ERBB3, ERBB4, EGFRvIII)); neural cell adhesion molecule (NCAM); carbonic anhydrase IX (CAIX); LMP2; ephrin A receptor 2 (EphA2); fucosyl GM; sialyl Lewis adhesion molecule (sLe); ganglioside GM3; TGS5; high molecular weight melanoma-associated antigen (HMW-MAA); o-acetyl GD2 ganglioside; folate receptor; tumor vascular endothelial marker 1 (TEM1/CD248); tumor vascular endothelial marker 7 related (TEM7R); claudin 6, claudin 18.2, claudin 18.1; ASGPR1; CDH16; 5T4; 8H9; αvβ6 integrin; B cell maturation antigen (BCMA); CA9; kappa light chain; CSPG4; EGP2, EGP40; FAP; FAR; FBP; embryonic AchR; HLA-A1, HLA-A2; MAGEA1, MAGE3; KDR; MCSP; NKG2D ligand; PSC1; ROR1; Sp17; SURVIVIN; TAG72; TEM1; fibronectin; tenascin; carcinoembryonic variant of tumor necrosis zone; G protein-coupled receptor family C group 5-member D (GPRC5D); X chromosome open reading frame 61 (CXORF61); CD97; CD179a; anaplastic lymphoma kinase (ALK); polysialic acid; placental-specific 1 (PLAC1); hexose part of globoH glycoceramide (GloboH); breast differentiation antigen (NY-BR-1); uroplakin 2 (UPK2); Hepatitis A virus cell receptor 1 (HAVCRi); adrenergic receptor 3 (ADRB3); pannexin 3 (PANX3); G protein coupled receptor 20 (GPR20); lymphocyte antigen 6 complex locus K9 (LY6K); olfactory receptor 51E2 (OR51E2); TCRγ alternating reading frame protein (TARP); Wilms tumor protein (WT1); ETS translocation variant gene 6 (ETV6-AML); sperm protein 17 (SPA17); X antigen family member 1A (XAGE1); angiopoietin binding cell surface receptor 2 (Tie2); melanoma cancer testis antigen-1 (MAD-CT-1); melanoma cancer testis antigen-2 (MAD-CT-2); Fos-related antigen 1; p53 mutant; human telomerase reverse transcriptase (hTERT); sarcoma translocation breakpoint; melanoma inhibitor of apoptosis (ML-IAP); ERG (transmembrane protease serine 2 (TMPRSS2) ETS fusion gene); N-acetylglucosaminyl transferase V (NA17); paired box protein Pax-3 (PAX3); androgen receptor; cyclin B1; V-myc avian myelocytomatosis viral oncogene neuroblastoma-derived homolog (MYCN); Ras homologue family member C (RhoC); cytochrome P450 1B1 (CYP1B1); CCCTC binding factor (zinc finger protein)-like (BORIS); squamous cell carcinoma antigen 3 (SART3) recognized by T cells; pairing box protein Pax-5 (PAX5); proacrosin binding protein sp32 (OYTES1); lymphocyte specific protein tyrosine kinase (LCK); A-kinase anchoring protein 4 (AKAP-4); synovial sarcoma X breakpoint 2 (SSX2); CD79a; CD79b; CD72; leukocyte-associated immunoglobulin-like receptor 1 (LAIR1); Fc fragment of IgA receptor (FCAR); leukocyte immunoglobulin-like receptor subfamily member 2 (LILRA2); CD300 molecular-like family member f (CD300LF); C-type lectin domain family 12 member A (CLEC12A); bone marrow stromal cell antigen 2 (BST2); EGF-like module containing mucin-like hormone receptor-like 2 (EMR2); lymphocyte antigen 75 (LY75); glypican-3 (GPC3); Fc receptor-like 5 (FCRL5); immunoglobulin lambda like polypeptide 1 (IGLL1).

The term "cancer" refers to a broad category of disorders characterized by hyperproliferative cell growth in vitro (e.g., transformed cells) or in vivo. The conditions that may be treated or prevented by the method of the present invention include, for example, various neoplasms, including benign or malignant tumors, various hyperplasias, and the like. The method of the present invention can achieve the inhibition and/or reversal of the undesirable hyperproliferative cell growth involved in such conditions. Cancers include but are not limited to: breast cancer, glioma, blood cancer, colon cancer, rectal cancer, renal cell carcinoma, liver cancer, lung cancer, small intestine cancer, esophageal cancer, melanoma, bone cancer, pancreatic cancer, skin cancer, head and neck cancer, skin or intraocular malignant melanoma, uterine cancer, ovarian cancer, rectal cancer, anal cancer, stomach cancer, testicular cancer, uterine cancer, fallopian tube cancer, endometrial cancer, cervical cancer, vagina cancer, vulva cancer, Hodgkin's disease, non-Hodgkin's lymphoma, endocrine system cancer, thyroid cancer, parathyroid cancer, adrenal cancer, soft tissue sarcoma, urethral cancer, penile cancer, childhood solid tumor, bladder cancer, renal or ureteral cancer, renal pelvis cancer, central nervous system (CNS) tumor, primary CNS lymphoma, tumor angiogenesis, spinal tumor, brainstem glioma, pituitary adenoma, Kaposi's sarcoma, epidermoid carcinoma, squamous cell carcinoma, T-cell lymphoma, environmentally induced cancer, a combination of the cancers, and the metastatic foci of the cancer.

The term "transfection" or "transduction" refers to the process of transferring or introducing exogenous nucleic acid into a host cell. A "transfected" or "transduced" cell is a cell that has been transfected, transformed or transduced with exogenous nucleic acid. The cells include primary subject cells and their progeny.

The terms "specifically bind" and "specifically recognize" have the same meaning herein, and refer to an antibody or ligand recognizing and binding an antigen (e.g., a tumor antigen) present in a sample, but the antibody or ligand basically will not recognize or bind other molecules in the sample.

As used herein, "refractory" refers to a disease (e.g., cancer) which does not respond to treatment. In some embodiments, refractory cancer may be resistant to treatment before or at the beginning of treatment. In other embodiments, refractory cancers may become resistant during treatment. Refractory cancers are also called resistant cancers. In the present invention, refractory cancers include but are not limited to: cancers that are not sensitive to radiotherapy, relapse after radiotherapy, are not sensitive to chemotherapy, relapse after chemotherapy, are not sensitive to CAR-T treatment, or relapse after treatment. Refractory or recurrent malignancies may treated by the treatment regimens described herein.

As used herein, "relapsed" refers to the return of the signs and symptoms of a disease (e.g. cancer) or a disease such as cancer during a period of improvement, for example, after a therapy, such as a previous treatment of cancer therapy.

The terms "individual" and "subject" have the same meaning herein, and may be humans or animals from other species.

The term "enhancement" refers to allowing a subject or tumor cell to improve its ability to respond to the treatment disclosed herein. For example, the enhanced response may include 5%, 10%, 15%, 20%, 25%, 30%, 35%, 40%, 45%, 50%, 55%, 60%, 65%, 70%, 75%, 80%, 85%, 90%, 95% or 98% or more enhancement of the responsiveness. As used herein, "enhancement" can also refer to increasing the number of subjects responding to treatment, such as immune effector cell therapy. For example, an enhanced response may refer to the total percentage of subjects responding to treatment, wherein the percentage is 5%, 10%, 15%, 20%, 25%, 30%, 35%, 40%, 45%, 50%, 55%, 60%, 65%, 70%, 75%, 80%, 85%, 90%, 95%, or 98%, or more.

In one aspect, the treatment is determined by the following clinical outcome or a combination thereof: increased, enhanced, or prolonged anti-tumor activity of T cells; increased number of anti-tumor T cells or the activated T cells, promoted secretion of IFN-γ and TNFα, as compared with the number before treatment. In another aspect, the clinical outcome is: tumor regression; tumor shrinkage; tumor necrosis; anti-tumor response through the immune system; tumor expansion, recurrence or spread or a combination thereof. In an additional aspect, the therapeutic effect is predicted by: the presence of T cells, the presence of genetic markers indicative of T cell inflammation, promotion of IFN-γ, TNFα secretion, or a combination thereof. In one aspect, treating a tumor includes reducing the growth, survival or viability of cancer cells through treatment.

The immune effector cells as disclosed herein may be administered to an individual by various routes, including, for example, orally or parenterally, e.g., intravenous, intramuscular, subcutaneous, intraorbital, intrasaccular, intraperitoneal, intrarectal, intracisternal, intratumoral intranasally, intradermal or passive or promoted absorption through the skin by using, for example, skin patch or transdermal iontophoresis, respectively.

The total amount of agent to be administered in practicing the method of the present invention may be administered to a subject as a single dose by bolus injection or by infusion over a relatively short period of time; or may be administered by using a graded treatment regimen, wherein multiple doses are administered over an extended period of time. Those skilled in the art will know that the amount of the composition for treating a pathological condition in a subject depends on many factors, including the age and general health of the subject, as well as the route of administration, and the number of treatments to be administered. Taking these factors into account, the technician will adjust the specific dosage as needed. In general, the phase I and phase II clinical trials are initially used to determine the formulation of the composition, the route and frequency of administration.

Range: various aspects of the invention may be presented in a range format throughout this disclosure. It should be understood that the description in range format is only for convenience and brevity, and should not be regarded as an unchangeable limitation on the scope of the present invention. Therefore, the description of a range should be considered to specifically disclose all possible subranges and individual values within that range. For example, the description of a range e.g., from 1 to 6, should be considered to specifically disclose subranges, such as 1 to 3, 1 to 4, 1 to 5, 2 to 4, 2 to 6, 3 to 6, etc., and individual values within the range for, such as 1, 2, 2.7, 3, 4, 5, 5.3, and 6. As another example, a range such as 95-99% identity includes a range with 95%, 96%, 97%, 98%, or 99% identity, and includes subranges such as 96-99%, 96-98%, 96-97%, 97-99%, 97-98% and 98-99% identity. This applies regardless of the width of the range.

According to the present disclosure, those skilled in the art should understand that many changes or modifications may be made in the disclosed specific embodiments, and still obtain the same or similar results without departing from the spirit and scope of the present invention. The scope of present invention is not limited to the specific embodiments described herein (which are only intended to exemplify various aspects of the present invention), and functionally equivalent methods and components are within the scope of the present invention. In fact, based on the foregoing description, various modifications of the present invention plus those shown and described herein will become apparent to those skilled in the art.

The present invention will be further illustrated below in conjunction with specific examples. It should be understood that these examples are only used to illustrate the present invention, and not to limit the scope of the present invention. In the following examples, the experimental methods without specific conditions usually adopt conventional conditions, for example, the conditions described in J. Sambrook et al., "Molecular Cloning Experiment Guide (Third Edition)" (Science Press, 2002), or the conditions recommended by the manufacturer.

Exemplary antigen receptors of the present invention, including CARs, and the methods for engineering and introducing a receptor into a cell, refer to, for example, those disclosed in Chinese patent application publication Nos. CN107058354A, CN107460201A, CN105194661A, CN105315375A, CN105713881A, CN106146666A, CN106519037A, CN106554414A, CN105331585A, CN106397593A, CN106467573A, CN104140974A, international patent application publication Nos. WO2017186121A1, WO2018006882A1, WO2015172339A8, and WO2018/018958A1.

Example 1: Construction of CAR-T Cells

Referring to the plasmid profile shown in FIG. 1A, a lentiviral plasmid PRRLSIN-hu9F2-28Z of the second-generation chimeric antigen receptor expressing humanized antibody hu9F2 (the nucleotide sequence is shown in SEQ ID NO: 5, and the amino acid sequence is shown in SEQ ID NO: 14) is constructed by using conventional methods of molecular biology in the field.

The antibody hu9F2 has HCDR1, HCDR2, HCDR3 respectively represented by SEQ ID NOs: 15, 16, 17, and LCDR1, LCDR2, LCDR3 respectively represented by SEQ ID NOs: 18, 19, 20.

The Hu9F2-28Z sequence consists of: CD8a signal peptide (SEQ ID NO: 6), hu9F2scFv (SEQ ID NO: 5), CD8 hinge (SEQ ID NO: 7), CD28 transmembrane domain (SEQ ID NO: 10) and intracellular signaling domain (SEQ ID NO: 8), and the intracellular fragment of CD3 (CD3ζ; SEQ ID NO: 9). PRRLSIN-hu9F2-28Z is transfected into 293T packaging lentivirus to obtain lentivirus.

Figure 1B:
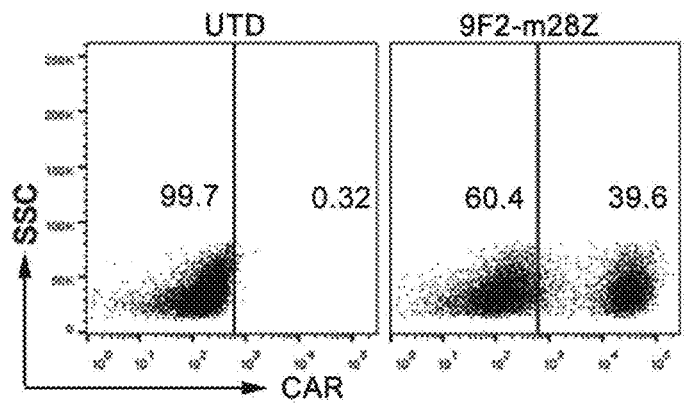
FIG. 1B is the detection of the positive rate of CAR T cells.

T cell activation: human PBMCs are cultured in AIM-V medium, adding 2% human serum type AB and 500 U/mL recombinant human IL-2, and adding CD3/CD28 antibody combined with magnetic beads for 48h activation. The resulting lentiviruses are used to infect the activated T cells to obtain hu9F2-28Z CART cells. The flow cytometry results are shown in FIG. 1B, and the CAR sequence is shown in SEQ ID NO: 22.

Example 2: Detection of the Toxicity of Sorafenib on Liver Cancer Cells and CAR-T Cells by CCK8 Assay The hu9F2-28Z CAR T cells in Example 1 are taken to spread them in a 96-well plate, 4×10$^4$ cells per well, 100 ul of media. Liver cancer cells PLC/RPF/5 (low GPC3 expression), SK-HEP-1 (no GPC3 expression), and Huh7 (high GPC3 expression) are taken to spread them in a 96-well plate, 4000 cells per well, 100 ul medium. Different concentrations of sorafenib are taken to add it into the cells respectively, so as to make six gradients (i.e., 10 μM, 5 μM, 1 μM, 0.5 μM, 0.1 μM, and 0 μM; wherein 10 μM, 5 μM, 1 μM, 0.5 μM, 0.1 μM is the dosing group, 0 μM 1 is the non-dosing group), in addition, a set of wells with medium only is set up as the blank group. After 48h, 10 ul of CCK8 reagent (Dojindo company) is added into each well, incubating at 37° C. for 1 hour, then measuring the absorbance at 450 nm with a microplate reader and calculating the cell viability respectively.

The calculation formula is: cell viability (%) [A (dosing)–A (blank)]/[A (non-dosing)–A (blank)]

Figure 2:
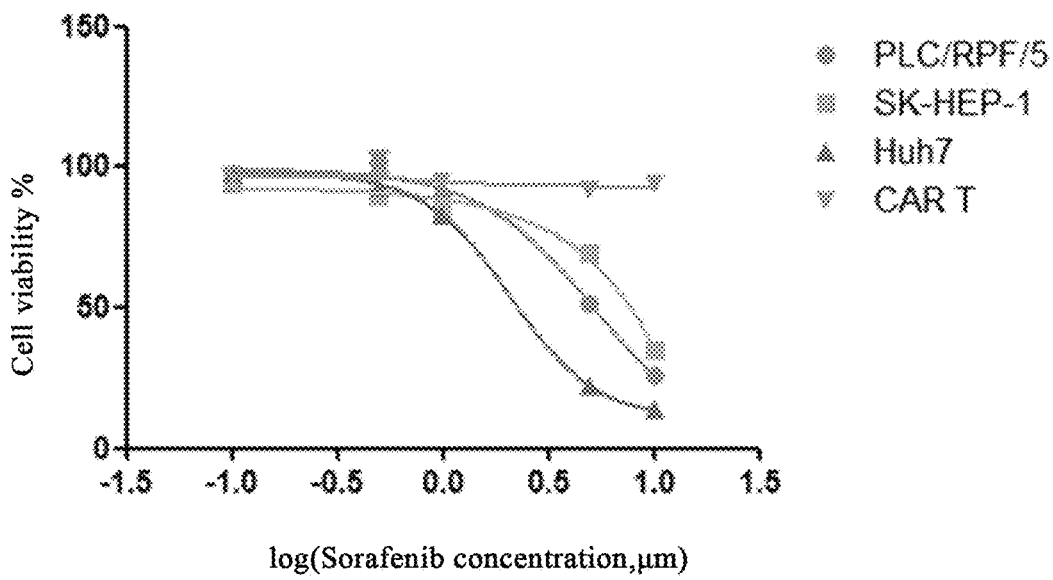
FIG. 2 shows the toxicity test of sorafenib on liver cancer cells and CAR T cells.

The results are shown in FIG. 2. Sorafenib has no obvious inhibitory effect on CAR T cells.

Example 3: The Killing Activity of CAR T Cells on Tumor Cells Pretreated with Sorafenib Different concentrations of sorafenib (1 μM, 0.1 μM, and 0 μM) are added to the culture medium containing Huh7 cells, digesting with trypsin after incubation at 37° C. for 24 hours, and then the remaining drug is washed with PBS. The hu9F2-28Z CAR T cells in Example 1 are taken to incubate with the Huh7 cells pretreated with different concentrations of sorafenib at a ratio of 1:1, and 18 hours later, the killing of hu9F2-28Z CAR T cells on tumor cells pretreated with different concentrations of sorafenib is detected by Cytox 96 Non-Radioactive Cytotoxicity Assay (Promaga, REF: G1782).

Figure 3:
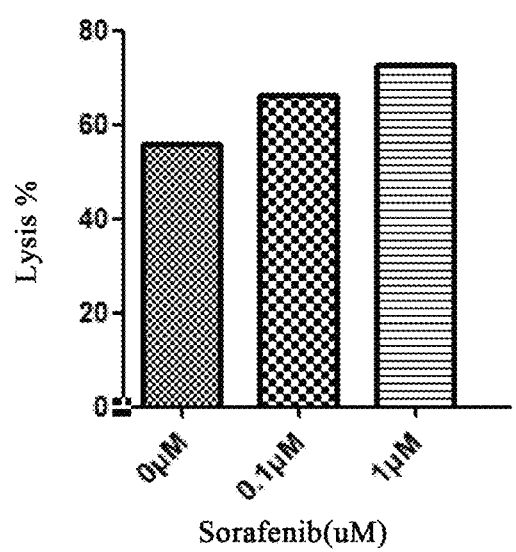
FIG. 3 shows the in vitro detection of the killing ability of CAR T cells on tumor cells treated with sorafenib.

The results are shown in FIG. 3. Compared with the group without sorafenib, the killing sensitivity of tumor cells treated with 0.1 M sorafenib to CAR T cells is increased by 11%, and the killing sensitivity of tumor cells treated with 1 M sorafenib to CAR T cells is increased by 16.8%.

Example 4: Inhibitory Effect of the Combination of Sorafenib and CAR T Cells on Hepa1-6-GPC3 Subcutaneous Tumor In this example, mouse gene sequences are used to construct the transmembrane domain and intracellular domain of CAR. C57BL/6 mice (mice with normal immune system) are divided into 5 groups:

Vehicle group: Sorafenib is not given;
Sorafenib group: Sorafenib alone is administrated;
CAR T+vehicle group: hu9F2-m28Z CAR T cells and solvent are administrated;
UTD+sorafenib group: T cells not infected with CAR and sorafenib are administrated;
CAR T+sorafenib group: hu9F2-m28Z CAR T cells and sorafenib are administrated.

Figure 4:
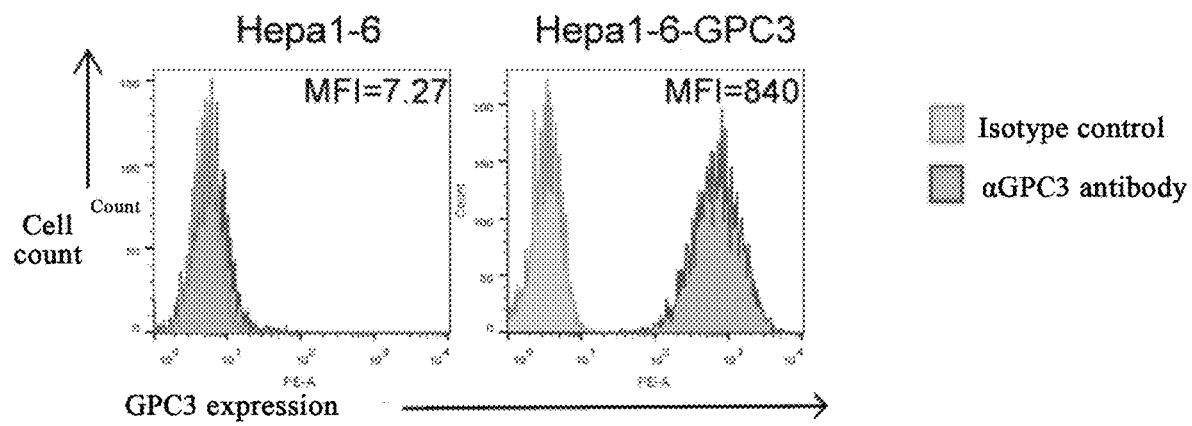
FIG. 4 shows the flow cytometric detection of GPC3 expression on Hepa1-6 cells.

1. A mouse liver cancer cell Hepa1 cell model (Hepa1-6-GPC3) overexpressing human-mouse chimeric GPC3 (SEQ ID NO: 11) is established by conventional methods of molecular biology. As shown in FIG. 4, Hepa1-6 cells overexpressing GPC3 are confirmed by flow cytometry.

2. Hepa1-6-GPC3 cells in the logarithmic growth phase and growing well are collected, inoculating 1×10$^7$ target cells under the right axilla of C57BL/6 mice (mice with normal immune system).

3. On the 4th day after tumor inoculation, T lymphocytes from mouse spleen are taken to construct hu9F2-m28Z CAR T cells. The construction method is as follows:

The coding sequence of mouse CD8a signal peptide (SEQ ID NO: 4), hu9F2scFv (SEQ ID NO: 5), the coding sequence of mouse CD8a hinge domain and transmembrane domain (SEQ ID NO: 1), the coding sequence of mouse CD28 intracellular domain (SEQ ID NO: 2), and the coding sequence of the mouse CD3ζ intracellular domain (SEQ ID NO: 3) are connected in sequence, and the hu9F2-m28Z gene fragment is obtained by in vitro gene synthesis, and the IRES-GFP fragment in the retroviral vector MSCV-IRES-GFP (purchased from Addgene) is replaced by MluI and SalI double cleavage sites to obtain the recombinant vector MSCV-hu9F2-m28Z. 293T cells are infected with MSCV-hu9F2-m28Z to obtain packaged retrovirus.

T lymphocytes from mouse spleen are taken and activated with Dynabeads Mouse T-activator CD3/CD28, adding retrovirus to infect for 12 hours after activation, so as to obtain hu9F2-m28Z CAR T cells.

4. On the 7th day after tumor inoculation, sorafenib or solvent is administered: dissolving sorafenib in a solvent (5% DMSO, 45% PEG400, 50% H$_2$0), for the sorafenib group, UTD+sorafenib group, and CAR T+sorafenib group, the mice are intragastrically administered with a dose of 7.5 mg/kg per mouse. For the vehicle group and CAR T+vehicle group, the mice are intragastrically administered with solvent. The first administration of sorafenib is recorded as day 0, and sorafenib is administered once a day for 5 consecutive days.

5. On the 8th day after tumor inoculation, for the CAR T+vehicle group and CAR T+sorafenib group, each mouse is administered 3*10⁶ hu9F2-m28Z CAR T cells; for the UTD+sorafenib group, each mouse is administered 3*10⁶ T cells not infected with CAR.

Figure 5:
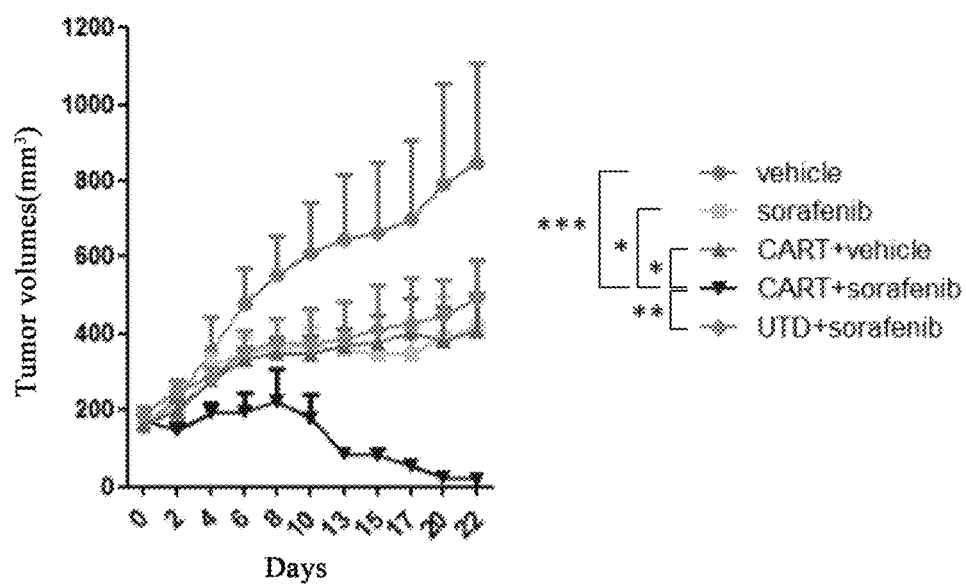
FIG. 5 shows the inhibitory effect of sorafenib in combination with CAR T cells on the tumor volume of hepa1-6-GPC3 subcutaneous tumors.

The changes in tumor volume are observed continuously and measure three times a week, the calculation formula for tumor volume is: (length*width$^2$)/2. The detection results of the tumor volume are shown in FIG. 5. Compared with other groups, the CAR T+sorafenib group has a significant effect of inhibiting tumor growth (Two-way ANOVA with Bonferroni post-tests, * means $p<0.05$,  means $p<0.01$, * means $p<0.001$).

Figure 6:
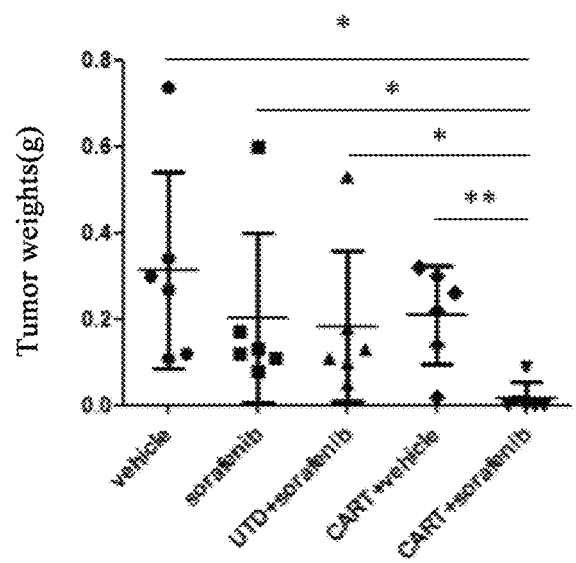
FIG. 6 shows the inhibitory effect of sorafenib in combination with CAR T cells on the tumor weight of hepa1-6-GPC3 subcutaneous tumors.

22 days after treatment, the tumors disappear in 4 out of 6 mice in the CAR T+sorafenib combination therapy group, while the tumors do not disappear in any mouse in the other groups. The mice are sacrificed by pulling the neck 22 days after treatment (i.e., Day 22), the subcutaneous tumors of the mice are peeled off and weighed, and the results are shown in FIG. 6. The results show that as compared with the vehicle group, the sorafenib group, and the CAR T+vehicle group and the UTD+sorafenib group, the CAR T+sorafenib combination therapy group has a significant tumor inhibitory effect (Unpaired test, * means $p<0.05$,  means $p<0.01$, * means $p<0.001$).

Figure 7A:
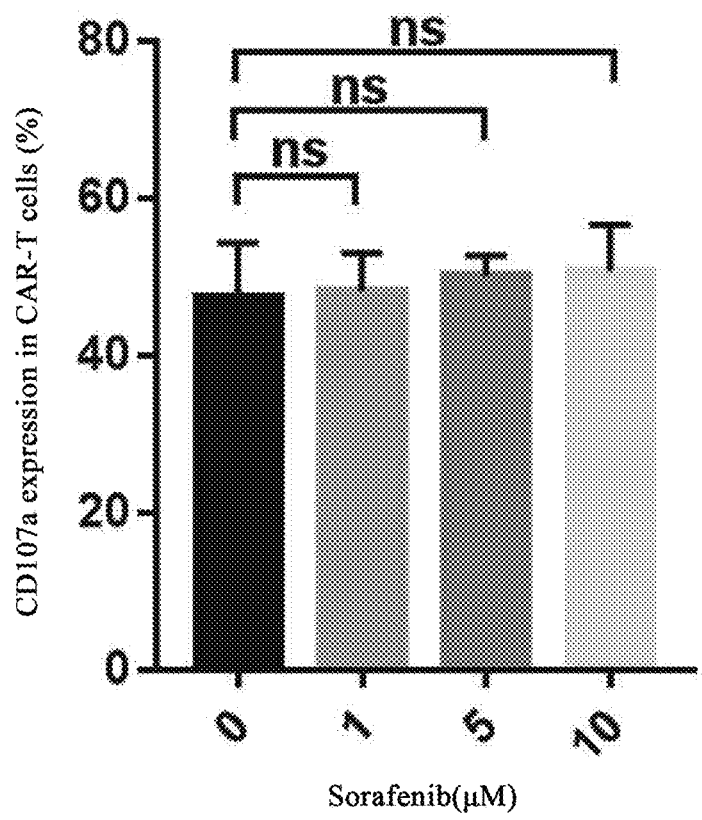
FIG. 7 shows the in vitro detection of the degranulation ability (FIG. 7A), proliferation ability (FIG. 7B) and killing ability (FIG. 7C) of CAR T cells treated with sorafenib.

Example 5: Detection of the Effect of Sorafenib on the Degranulation, Proliferation and Killing of CAR T Cells 1. The Effect of Sorafenib on the Degranulation Marker CD107a After co-incubating the hu9F2-28Z CAR T cells in Example 1 with different concentrations of sorafenib and PLC/RPF/5 cells for 24 hours, the treated CAR T cells are collected and incubated with anti-human CD107a-PerCP antibody (eBioscience) and GPC3 tagged protein with GFP fluorescent protein; PerCP and GFP fluorescence intensity are detected by flow cytometry, representing the expression of human CD107a and CAR, respectively. The results are shown in FIG. 7A, and there is no significant change between the expression ability of CD107a in the sorafenib-free group and in the sorafenib treatment group.

2. The Effect of Sorafenib on CAR T Cell Proliferation

CellTrace Violet kit (Thermofisher) is used to monitor cell proliferation at different generations. Hu9F2-28Z CAR T cells are taken to add into CellTrace dye working solution, incubating at 37° C. to neutralize the dye.

The hu9F2-28Z CAR T cells treated above and PLC/RPF/5 cells are spread in a 24-well plate at a ratio of 1:1, then different concentrations of sorafenib (0, 1, 5, 10 M) are added, co-incubating for 24 hours, and each group has 3 replicate holes.

Figure 7B:
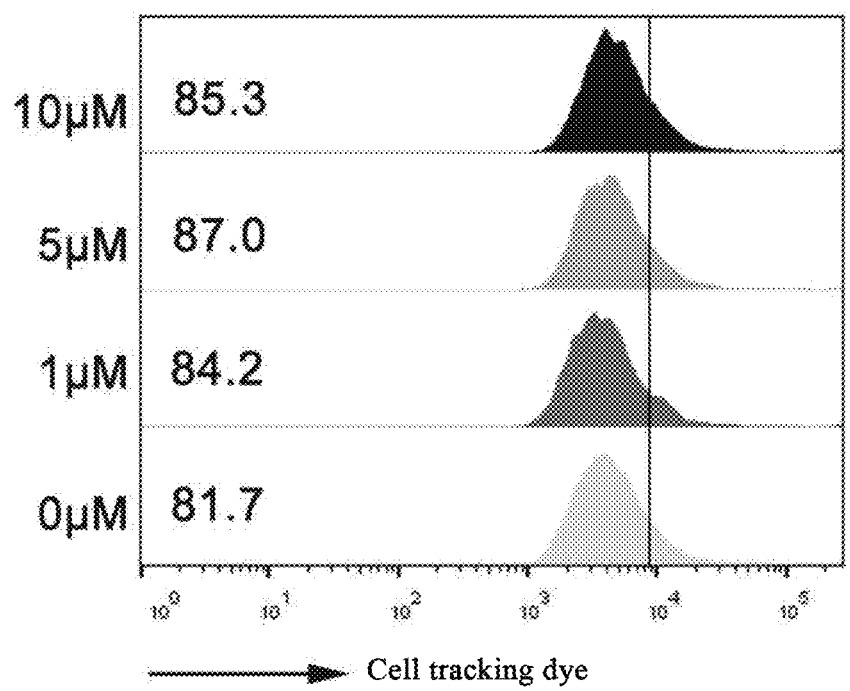

Cells in each group are detected by flow cytometry, and the results of sorafenib are shown in FIG. 7B. After co-incubating the sorafenib-free group and the sorafenib treatment group respectively with GPC3-expressing tumor cells, the proliferation ability of CAR T cells do not change significantly.

3. In Vitro Cytotoxicity Test a) PLC/RPF/5 cells are used as target cells, and hu9F2-28Z CAR T cells in Example 1 are effector cells. An appropriate amount of hu9F2-28Z CAR T cells are taken and treated with different concentrations of sorafenib (0, 1, 5, 10 M) for 4 hours, then collecting them by centrifugation.

Plating cells in the experimental group: the number of target cells is 10000 cells/well, and the effector cells are hu9F2-28Z CAR T cells treated with sorafenib. The effector to target ratios (E/T) are 20:1, 10:1, 5:1, 2.5:1, and different numbers of effector cells are added according to different effector to target ratios. Each group has 5 replicate holes.

Plating cells in the control group: this experiment also needs to set up other control groups to eliminate the interference of LDH spontaneously released from effector cells and target cells, and the interference of LDH contained in the medium; they are respectively: the control group with maximum released LDH from target cells; the control group with spontaneously released LDH from target cells; the control group with spontaneously released LDH from effector cells; blank medium background group; and blank medium background added with lysis solution group. Each group has 5 replicate holes.

After the above-mentioned cells are plated, they are incubated in a constant temperature incubator at 37° C. and 5% $CO_2$, and then transferred to an enzyme-labeled plate for substrate color development. The absorbance at 490 nm is measured with a microplate reader to calculate the cell killing toxicity.

b) The calculation formula is: cytotoxicity (%)=(experimental group−effector cell spontaneous group−target cell spontaneous group−background group)/(target cell maximum group−target cell spontaneous group−lysis solution background group).

Figure 7C:
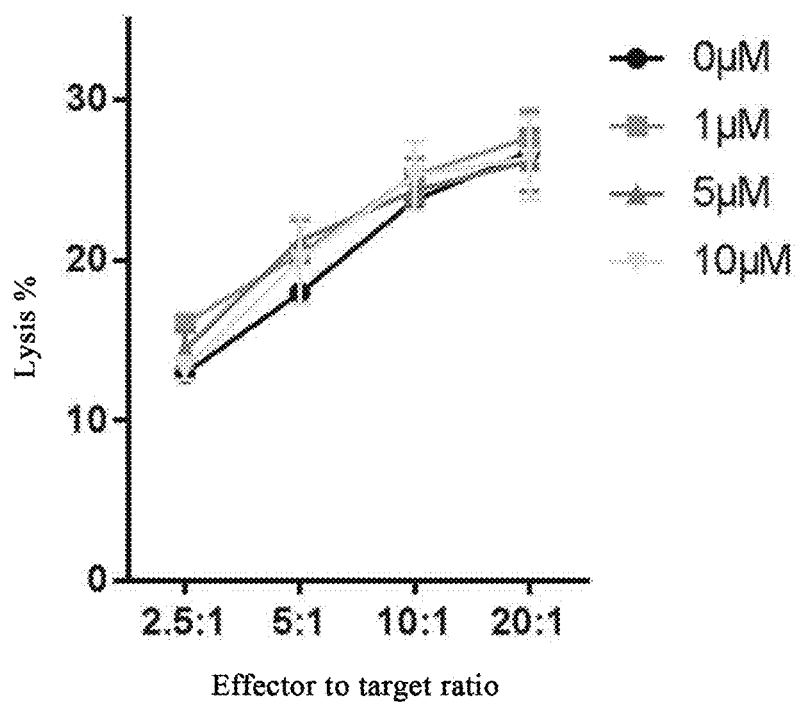

The results are shown in FIG. 7C, the killing toxicity of hu9F2-28Z CAR T cells treated with sorafenib on GPC3-positive tumor cells do not change significantly.

The above results indicate that sorafenib does not affect the degranulation ability, proliferation and killing toxicity of CAR T cells.

Example 6: Effect of Sorafenib on Cytokine Secretion of CAR T Cells

As for the specific steps, referring to the steps in the manual of The Cytometric Bead Array System (BD, USA), which are briefly described as follows:

a) Collecting the supernatant: 1×10⁵ hu9F2-28Z CAR T cells in Example 1 are spread on 24-well plate coated with the GPC3 proteins, adding different concentrations of sorafenib (0, 1, 5, 10 μM) for treatment, incubating in an incubator at 37° C., 5% $CO_2$, and then centrifuging to collect the cell supernatant, the concentrations of human cytokine IL2, IFN-γ, and TNF-α in it are detected.

b) The microspheres (cytometric bead array system, BD, USA) capturing the human cytokine IL2, IFN-γ, and TNF-α are taken to mix in a suspension.

c) The mixture of the microspheres for capturing and detection antibody are added into the standard or supernatant sample, incubating at room temperature in the dark; after the incubation is completed, it is washed with washing buffer, then centrifuging, and discarding the supernatant.

Figure 8A:
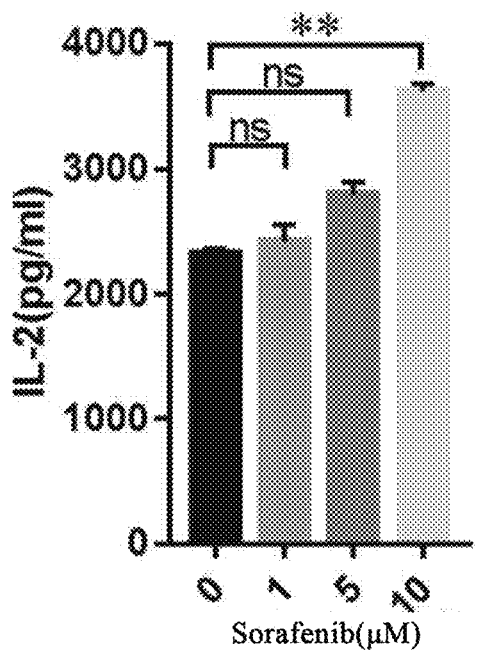
FIG. 8 shows detecting the effect of sorafenib on the cytokine secretion of human CAR T cells, i.e., IL-2 (FIG. 8A), IFN-γ (FIG. 8B) and TNF-α (FIG. 8C).
Figure 8B:
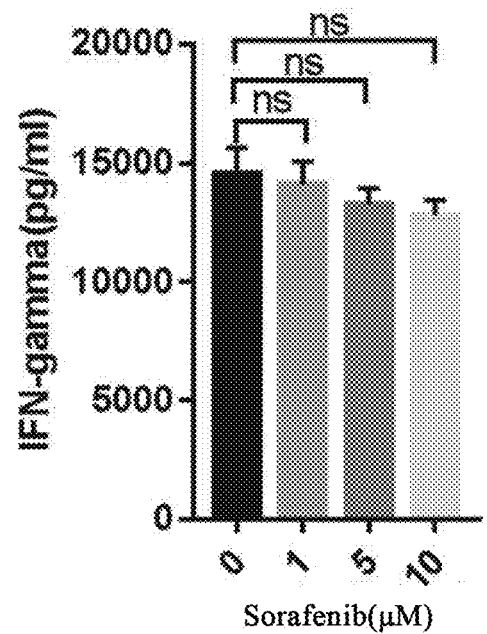
Figure 8C:
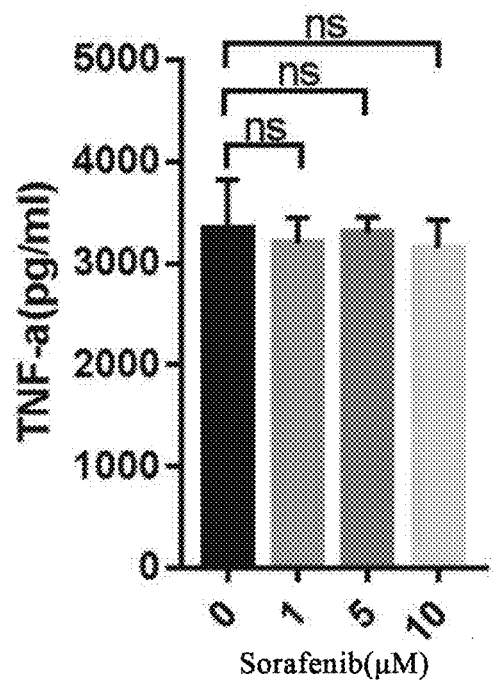

The secretion levels of IL-2, IFN-γ and TNF-α are detected by flow cytometry, and the results are shown in FIGS. 8A, 8B, and 8C, wherein ns means $p>0.05$; *$p<0.05$; $p<0.01$; *$p<0.001$, one-way ANOVA.

Example 7: Treatment of Liver Cancer by Combination of Sorafenib and Human CAR T Cells 1. Establishing a transplanted tumor model of human liver cancer cells: 5×10⁶ cells of PLC/RPF/5 cells in logarithmic growth phase are inoculated into the subaxillary skin of NSG mice. The day of inoculation is the 0$^{th}$ day (Day0).

2. The 11$^{th}$ day (Day11): the volume of mouse subcutaneous tumor is about 150 mm$^3$, and the mice are randomly divided into 6 groups according to the tumor volume with 5-6 mice in each group. Sorafenib is dissolved in a solvent (5% DMSO, 45% PEG400, 50% $H_2O$). Solvent is administrated to the sorafenib-free group.

(1) Control group (vehicle): the solvent is administrated on Day 11, once a day, and the volume administrated is the same as that in the experimental group, for two weeks.

(2) Single treatment group (3 groups in total):
Sora 7.5: on Day 11, mice are intragastically administrated with sorafenib at 7.5 mg/kg, once a day for two weeks.
Sora 30: on Day 11, mice are intragastically administrated with sorafenib at 30 mg/kg, once a day for two weeks.
CAR+vehicle: on Day11, the solvent is administrated once a day, and the volume administrated is the same as that in the experimental group for two weeks; and on the same day (Day11), after the solvent is administrated, $2 \times 10^6$ hu9F2-28Z CAR T cells in Example 1 are injected through tail vein.

(3) Combination therapy group (2 groups in total):
CAR+Sora7.5: on Day11, mice are intragastically administrated with sorafenib at 7.5 mg/kg, once a day for two weeks; and on the same day (Day11), after sorafenib is administered, $2 \times 10^6$ hu9F2-28Z CAR T cells in Example 1 are injected through tail vein.
CAR+Sora30: on Day11, mice are intragastically administrated with sorafenib at 30 mg/kg, once a day for two weeks; and on the same day (Day11), after sorafenib is administered, $2 \times 10^6$ hu9F2-28Z CAR T cells in Example 1 are injected through tail vein.

Figure 9A:
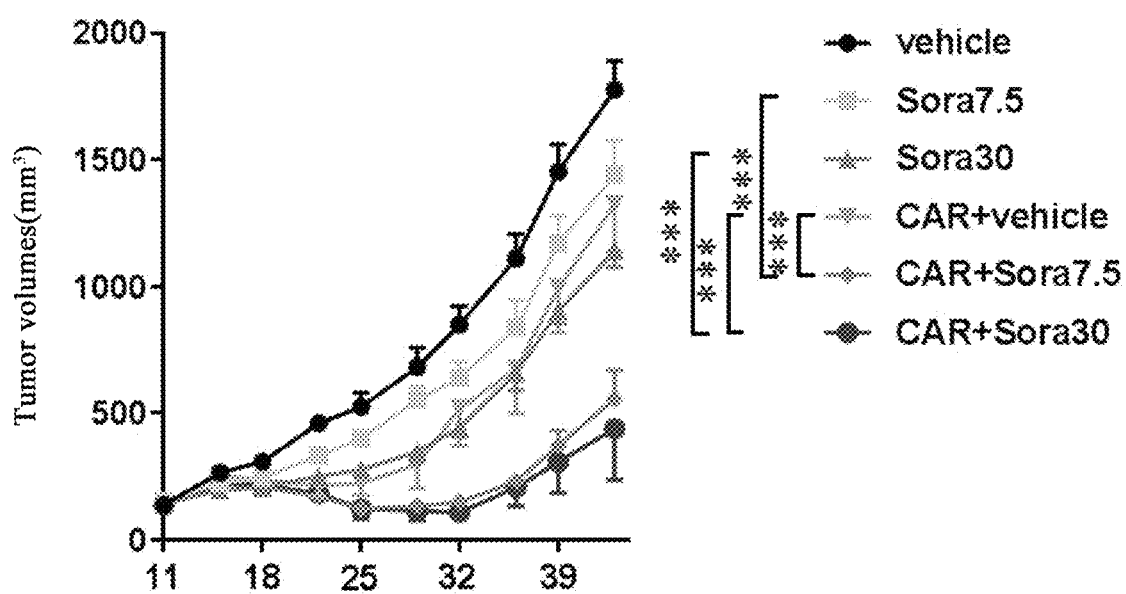
FIG. 9 shows the tumor volume (9A) and tumor weight (9B) of the treatment of liver cancer by using sorafenib in combination with human CAR T cells.

3. The volume changes of subcutaneous tumors in mice are measured and recorded twice a week. The calculation formula for tumor volume is: tumor volume=(tumor length x tumor width$^2$)/2. The results are shown in FIG. 9A, compared with the single treatment group, the combination therapy of sorafenib and hu9F2-28Z CAR T cells can significantly inhibit tumor growth (P<0.001, 2-way ANOVA).

The tumor inhibitory rate is calculated with reference to the control group. On the 43$^{rd}$ day (Day 43) after tumor inoculation, the tumor inhibitory rate of each group is respectively 18.8% for Sora 7.5, 35.8% for Sora30, 25.3% for CAR+vehicle, 68.7% for CAR+Sora7.5, and 75.2% for CAR+Sora30.

Figure 9B:
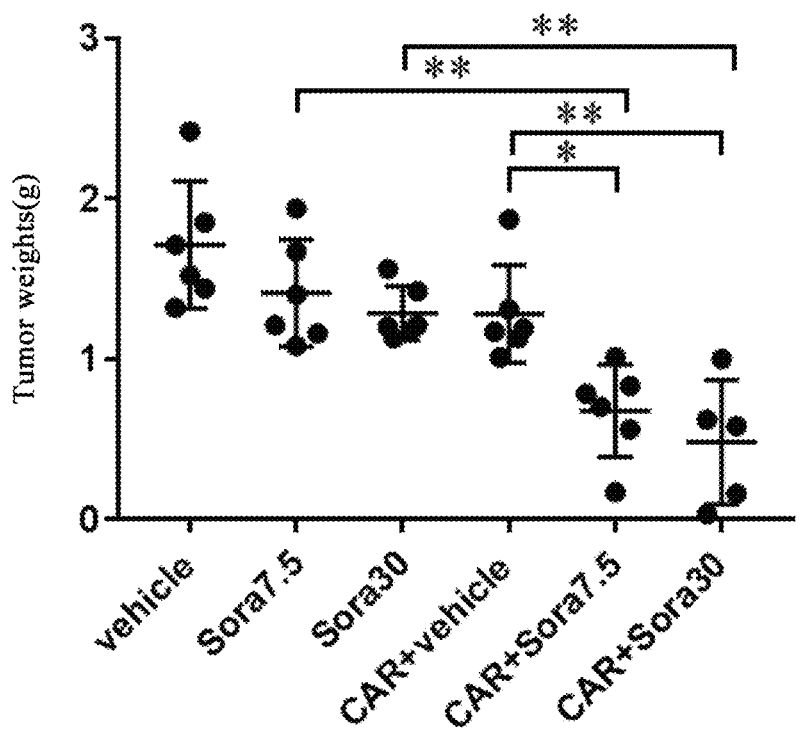

On the 43th day (Day 43), the mice are euthanized, and the subcutaneous tumors are stripped and weighed. The results are shown in FIG. 9B. Compared with the single treatment group, the tumor weights of the combination therapy of sorafenib and hu9F2-28Z CAR T cells (7.5 mg/kg or 30 mg/kg) are significantly reduced (*$p<0.05$; $p<0.01$, or *$p<0.001$, one-way ANOVA).

4. CAR T cell infiltration in the tumor and intratumor cell apoptosis

1) The tumor tissues of the euthanized mice are made into tissue sections by a conventional preparation method of tissue sections.

Figure 10A:
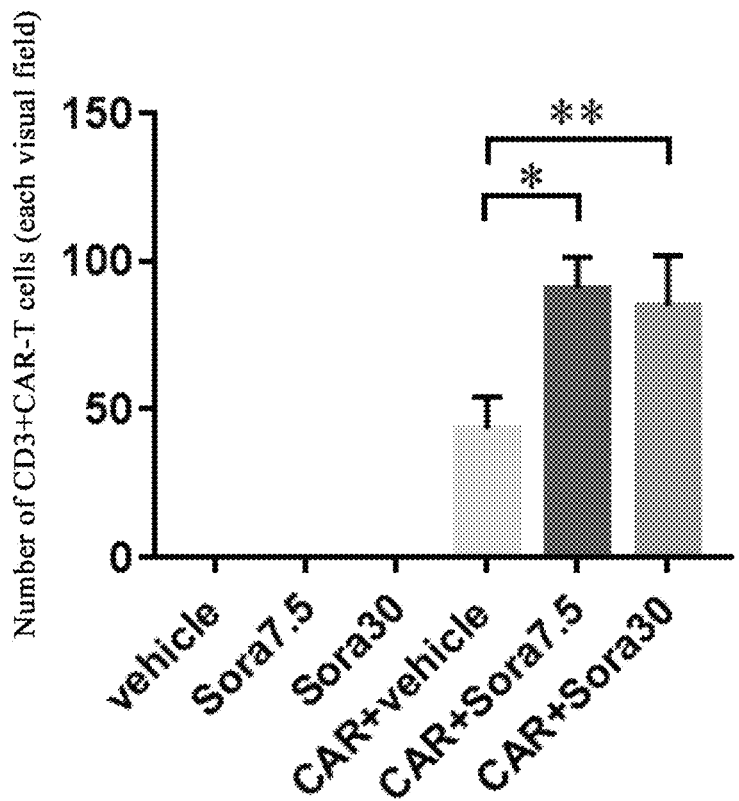
FIG. 10 shows the infiltration of CAR T cells into the tumor (FIG. 10A) and apoptosis (FIGS. 10B and 10C).

2) Anti-human CD3 antibody (Thermo Scientific) is used to detect human CAR T cells in the tumor tissue sections prepared in step 1). The results are shown in FIG. 10A. Compared with mice treated with hu9F2-28Z CAR T cells alone, there are more CD3+ human CAR T cells in the tumor tissues of the mice treated with combination of hu9F2-28Z CAR T cells and sorafenib (7.5 mg/kg, or 30 mg/kg) (*$p<0.05$; **$p<0.01$, one-way ANOVA), no CD3+ human CAR T cells staining are observed in the group that do not receive hu9F2-28Z CAR T cell treatment. The results show that sorafenib can promote the infiltration of CAR T cells in tumor tissues.

3) Anti-cleaved caspase-3 antibody (Cell Signaling Technology) is used to detect the apoptotic cells in the tumor tissue sections in step 1

Figure 10B:
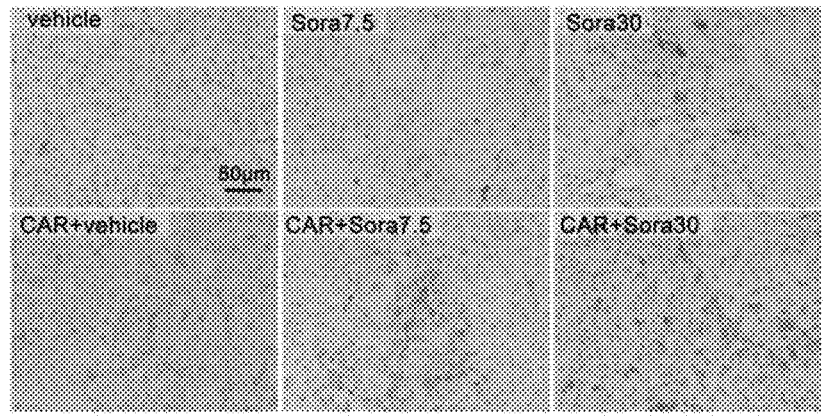

The tissue sections are stained by immunohistochemistry, and the nuclei in the tumor tissues are counterstained with hematoxylin. The results are shown in FIG. 10B. Compared with the control group and the mice treated with hu9F2-28Z CAR T cells alone, there are more cleaved caspase-3 positive cells in the tumor tissues of the mice treated with combination therapy of hu9F2-28Z Mice CAR T cells and sorafenib (7.5 mg/kg, or 30 mg/kg).

Figure 10C:
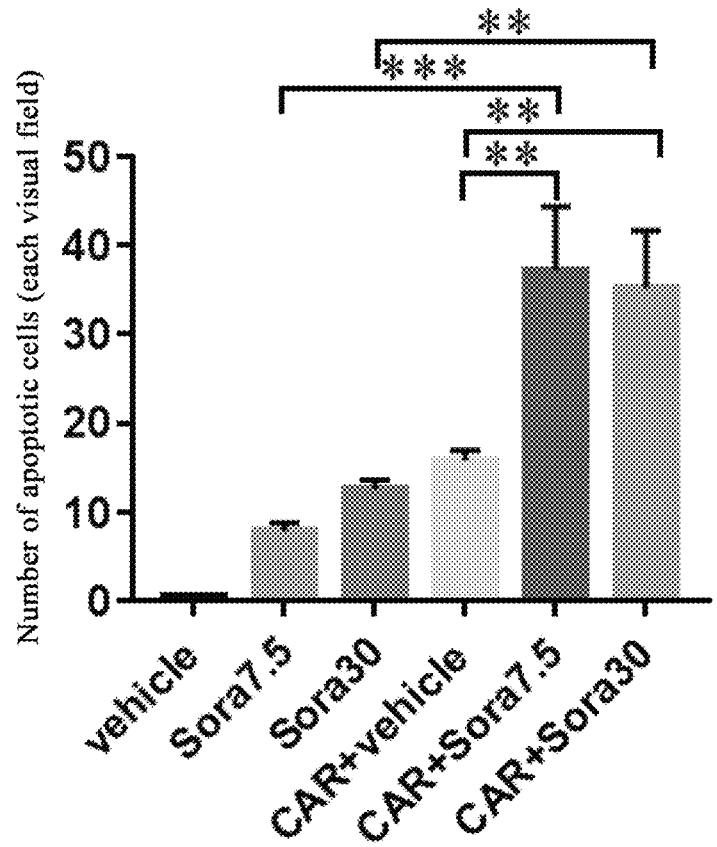

A total of 5 different visual fields in the tumor sections of two mice are used for observation and statistics. The results are shown in FIG. 10C, when sorafenib and CAR T cells are used in combination, the number of tumor cells undergoing apoptosis increases significantly ($p<0.01$, *$p<0.001$, one-way ANOVA).

Example 8: In Vitro Detection of the Synergy Between Sorafenib and Human CAR T Cells Referring to the experimental operations of the CellTrace Violet kit, the human liver cancer cells PLC/RPF/5 are labelled with CellTrace dye. The labeled PLC/RPF/5 are mix with hu9F2-28z CAR T cells at a ratio of 1:1, adding different concentrations of sorafenib (0, 1, 5, 10 μM) and incubating in a cell culture incubator for 48 hours; then the cells are centrifuged and collected, the cell pellet is resuspended in the staining buffer of the FITC Annexin V Apoptosis Detection Kit (purchased from BD), and then Annexin V-FITC dye is added for staining. On-board testing: the stained cells are collected by centrifugation, resuspending in staining buffer, then performing flow cytometry. The violet light signal is collected in the BV421 channel, which represents all tumor cells. Green light is collected in the FITC channel, which represents tumor cells undergoing apoptosis. FlowJo software is used to process the data.

Figure 11:
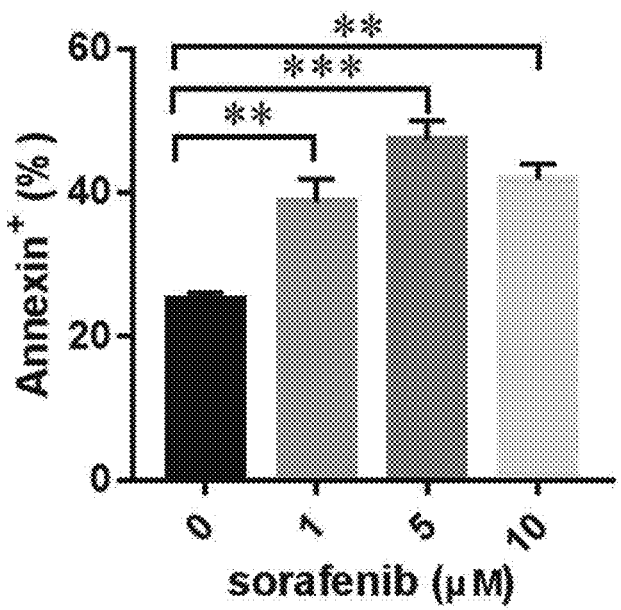
FIG. 11 shows the in vitro detection of the synergetic promotion of apoptosis of PLC/RPF/5 cells by sorafenib in combination with human CAR T cells.

The results are shown in FIG. 11, after the combination therapy of hu9F2-28Z CAR T cells and sorafenib, the apoptosis ratio of tumor cells is increased significantly, and the number of tumor cells undergoing apoptosis is also increased significantly (*$p<0.05$; $p<0.01$, or *$p<0.001$, one-way ANOVA).

The above in vitro experimental results indicate that, the combination therapy of sorafenib and CAR T cells can synergistically promote tumor cell apoptosis.

Example 9: The Effect of Combination of CAR T Cells and Regorafenib on the Treatment of Transplanted Tumor of Liver Cancer in Mice With reference to the operations in Example 4, a transplanted tumor model of Hepa1-6-chGPC3 cell C57BL/6 and hu9F2-m28Z CAR T cells are constructed.

On the 8th day after tumor cell implantation, the mice are randomly divided into three groups according to the tumor volumes. The mice in the regorafenib treatment group and the regorafenib+CAR T combination therapy group are intragastically administrated with regorafenib at 10 mg/kg, and the control group is administrated with the solvent, once a day, for ten days.

Figure 12:
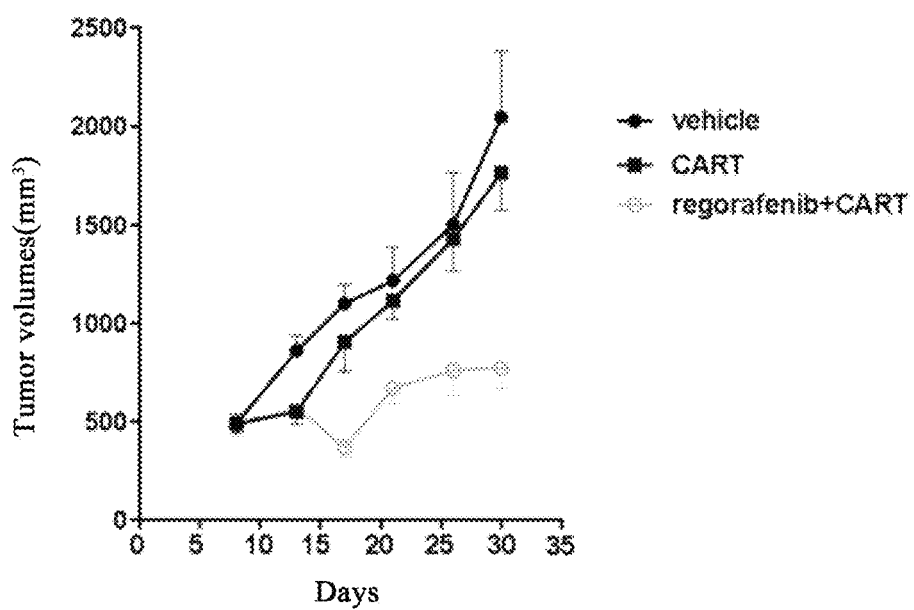
FIG. 12 shows the therapeutic results of CAR T cells in combination with regorafenib on the transplanted tumor of liver cancer in mice.

On the 9th day after tumor cell implantation, mice in the CAR T treatment group and the regorafenib+CAR T combination therapy group are injected with $2 \times 10^6$ CAR T cells through tail vein. After that, the mice are measured and recorded the volume changes of the subcutaneous tumors, twice a week. The results are shown in FIG. 12.

Example 10: Clinical Study on the Combination Therapy of Sorafenib and CAR T Cells Subject A is 60 years old, with weight body: 77 kg, and height: 170 cm. He is diagnosed with hepatocellular carcinoma and still in a progressive state after 7 months of surgical treatment. Immunohistochemistry shows GPC3 positive (70%, ++~+++). In this case, the patient receives the treatment of the technical solution according to the present invention.

After apheresis, the patient is administered continuously with oral sorafenib at a dose of 200 mg-400 mg at a time, twice per day (subjecting to the tolerable dose of the patient, for this Subject, 200 mg at a time), and administrated continuously every day.

Referring to the operations in Example 1, after infecting the patient's T cells with the lentivirus, hu9F2-28Z CAR T cells are prepared.

Two weeks after starting the administration of sorafenib, and before the administration of CAR-T cells, the patient receives lymphocyte clearance treatment, including fludarabine about 39 mg/day x 4 days (about 20 mg/m$^2$/day), and cyclophosphamide about 1000 mg/day x 2 days (about 500 mg/m$^2$/day).

Beginning on the third day after lymphocyte clearance treatment, approximately 5×10$^8$ CAR-T cells (approximately 6.49×10$^6$ CAR-T cells/kg patient body weight, and the total dose is approximately 1×10$^9$ CAR-T cells) are respectively administrated every day for two consecutive days.

On the third day after CAR-T cell administration, AFP is reduced by 35% as compared to that before CAR-T cell administration, and on the 13$^{th}$ day after CAR-T cell administration, AFP is reduced by 58.2% as compared to that before CAR-T cell administration.

Figure 13:
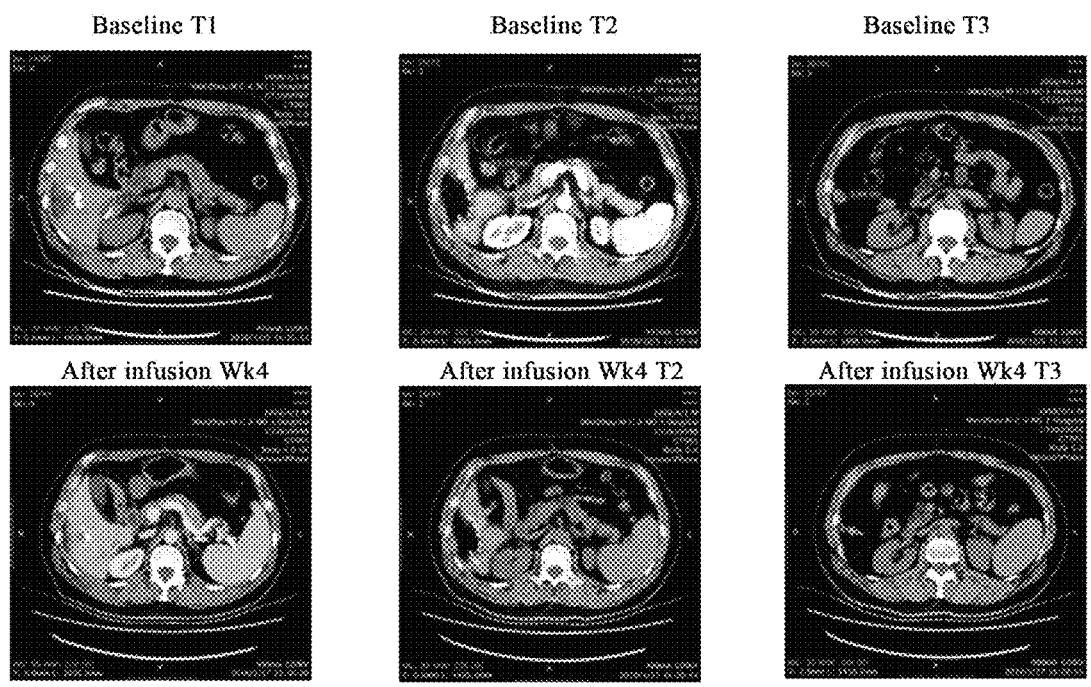
FIG. 13 shows the imaging pictures of subjects after treating by CAR T cells in combination with sorafenib.

After 4 weeks of treatment, the CT examination and imaging are shown in FIG. 13. Compared with the baseline, all the three possible target lesions are significantly reduced, reaching partial remission (PR) at a time point.

In the above examples, the CAR of CAR-T cells targeting GPC3 having the amino acid sequence shown in SEQ ID NO: 22 is adopted exemplarily. According to the teaching of the above examples, those skilled in the art may also use the amino acid sequence of SEQ ID NO: 21, 23, or 24.

In the above examples, CAR-T cells targeting GPC3 are adopted exemplarily. According to the teachings of this application, those skilled in the art may use CAR-T cells targeting other targets, such as CAR-T cells targeting EGFR (exemplarily, the sequence of scFv of CAR-T cells targeting EGFR is shown in SEQ ID NO: 12), and such as CAR-T cells targeting CLD18A2 (exemplarily, the sequence of scFv of CAR-T cells targeting CLD18A2 is shown in SEQ ID NO: 13).

The sequence information involved in the present invention is as follows:

| Names | SEQ ID NO: | Sequences |
|---|---|---|
| Hinge domain and transmembrane domain of mouse CD8α | 1 | actactaccaagccagtgctgcgaactccctcacctgtgcaccctaccgggacatctcagccccagagac cagaagattgtcggccccgtggctcagtgaaggggaccggattggacttcgcctgtgatatttacatctg ggcaccttggccggaatctgcgtggcccttctgctgtccttgatcatcactctcatctgctaccacagg agccga |
| Intracellullar domain of mouse CD28 | 2 | aatagtagaaggaacagactccttcaaagtgactacatgaacatgactccccggaggcctgggctcactc gaaagccttaccagccctacgcccctgccagagactttgcagcgtaccgcccc |
| Intracellullar domain of mouse CD3ζ | 3 | agcaggagtgcagagactgctgccaacctgcaggaccccaaccagctctacaatgagctcaatctagggc gaagagaggaatatgacgtcttggagaagaagcgggctcgggatccagagatgggaggcaaacagcagag gaggaggaaccccaggaaggcgtatacaatgcactgcagaaagacaagatggcagaagcctacagtgag atcggcacaaaaggcgagaggcggagaggcaaggggcacgatggcctttaccagggtctcagcactgcca ccaaggacacctatgatgccctgcatatgcagaccctggcc |
| Signal peptide of mouse CD8α | 4 | atggcctcaccgttgacccgctttctgtcgctgaacctgctgctgctgggtgagtcgattatcctgggga gtggagaagct |
| GPC3 scFv | 5 | gaggtgcagctggtgcagagcggcgccgaggtgaagaagcccggcgccagcgtgaaggtgagctgcaag gccagcggctacaccttcagcgactacgagatgcactgggtgcggcaggcccccggccagggcctggag tggatgggcgccatccaccccggcagcggcgacaccgcctacaaccagcggttcaagggccgggtgacc atcaccgccgacaagagcaccagcaccgcctacatggagctgagcagcctgcgggagcgaggacaccgcc gtgtactactgcgcccggttctacagctacgcctactggggccagggcaccctggtgaccgtgagcgcc ggtggaggcggttcaggcggaggtggttctggcggtggcggatcggacatcgtgatgacccagaccccc ctgagcctgccgtgacccccggcgagcccgccagcatcagctgccggagcagccagagcctggtgcac agcaacggcaacacctacctgcagtggtacctgcagaagcccggccagagccccagctgctgatctac aaggtgagcaaccggttcagcggcgtgcccgaccggttcagcggcagcggcagcggcaccgacttcacc ctgaagatcagccgggtggaggccgaggacgtgggcgtgtactactgcagccagagcatctacgtgccc tacaccttcggccagggcaccaagctggagatcaaacgt |
| Signal peptide of human CD8α | 6 | atggccttaccagtgaccgccttgctcctgccgctggccttgctgctccacgccgccaggccg |
| Hinge domain of human CD8α | 7 | accacgacgccagcgccgcgaccaccaacaccggcgcccaccatcgcgtcgcagcccctgtcctgcg cccagaggcgtgccggccagcggcggggggcgcagtgcacacgagggggctggacttcgcctgtgat |
| Intracellullar domain of human CD28 | 8 | aggagtaagaggagcaggctcctgcacagtgactacatgaacatgactccccgcgccccgggccaacc cgcaagcattaccagccctatgccccaccacgcgacttcgcagcctatcgctcc |

| Names | SEQ ID NO: | Sequences |
|---|---|---|
| Intracellullar domain of human CD3ζ | 9 | agagtgaagttcagcaggagcgcagacgcccccgcgtaccagcagggccagaaccagctctataacga gctcaatctaggacgaagagaggagtacgatgttttggacaagagacgtggccgggaccctgagatgg ggggaaaagccgcagagaaggaagaaccctcaggaaggcctgtacaatgaactgcagaaagataagatg gcggaggcctacagtgagattgggatgaaagcgagcgccggaggggcaaggggcacgatggccttta ccagggtctcagtacagccaccaaggacacctacgacgccatcacatgcaggccctgccccctcgc |
| Transmembrane domain of human CD28 | 10 | ttttgggtgctggtggtggttggtggagtcctggcttgctatagcttgctagtaacagtggcctttatt attttctgggtg |
| Human-mouse chimeric GPC3 | 11 | magtvrtacllvamllglgclgqaqppppdatchqyrsffqrlqpglkwvpetpvpgsdlqvclpkgptc c srkmeekyqltarlnmeqllqsasmelkfliiqnaavfqeafeivvrhaknytnamfknnypsltpqafef v gefftdvslyilgsdinvddmvnelfdslfpviytqmmnpglpesvldineclrgarrdlkvfgsfpklimt qvskslqvtriflqalnlgievinttdhlkfskdcgrmltrmwycsycqglmmvkpcggycnvvmqgc magv veidkywreyilsleelvngmyriydmenvllglfstihdsiqyvqknggkltttigklcahsqqrqyrsay ypedlfidkkilkvahveheetlssrrreliqklksfinfysalpgyicshspvaendtlcwnggelverys qkaarngmkqfnlhelkmkgpepvvsqiidklkhinqllrtmsvpkgkvldksldeeglesgdcgdde dec igssgdgmvkknqlrflaelaydldvddapgnsqqatpkdneistfhnlgnvhsplkilisvaiyvacfff lvh |
| EGFR-antibody | 12 | diqmtqspsslsasvgdrvtitchasqdinvnigwlqqkpgkafkgliyhgknledgvpsrfsgsgsgtdft ltisslqpedfatyycnqyenipltfgqgtkveikrggggsggggsggggsdvqlvesgglvqpggslrls cavsgysitsdyawnwirqapgkglewlgyisyrgrtqynpslksrisitrdnskntfflqlnslraedtav yycarmgknwdywgqgtlvtvss |
| 18A2-antibody | 13 | qvqlqesgpglikpsqtlsltctvsggsissgynwhwirqppgkglewigyihytgstnynpalrsrvtisv dtsknqfslklssvtaadtaiyycariyngnsfpywgqgttvtvssggggsggggsggggsdivmtqspds l avslgeratinckssqslfnsgnqknyltwyqqkpgqppkliiywastresgypdrfsgsgsgtdftltiss lqaedvavyycqnaysfpytfgggtkleikr |
| GPC3-antibody | 14 | evqlvqsgaevkkpgasvkvsckasgytfsdyemhwyrqapgqglewmgaihpgsgdtaynqrfkgr vtitad kststaymelsslrsedtavyycarfysyaywgqgtlvtvsaggggsggggsggggsdivmtqtplslpvt pg epasiscrssqslvhsngntylqwylqkpgqspqlliykvsnrfsgypdrfsgsgsgtdftlkisrveaedvg vyycsqsiyvpytfgqgtkleikr |
| GPC3-antibody HCDR1 | 15 | DYEMH |
| GPC3-antibody HCDR2 | 16 | AIHPGSGDTAYNQRFKG |
| GPC3-antibody HCDR3 | 17 | FYSYAY |
| GPC3-antibody LCDR1 | 18 | RSSQSLVHSNGNTYLQ |
| GPC3-antibody LCDR2 | 19 | KVSNRFS |
| GPC3-antibody LCDR3 | 20 | SQSIYVPYT |
| GPC3-CD3Z | 21 | evqlvqsgaevkkpgasykysckasgytfsdyemhwyrqapgqglewmgaihpgsgdtaynqrfkgr vtitadkststa ymelsslrsedtavyycarfysyaywgqgtlvtvsaggggsggggsggggsdivmtqtplslpvtpgepa siscrssqs lvhsngntylqwylqkpgqspqlliykvsnrfsgypdrfsgsgsgtdftlkisrveaedvgvyycsqsiyvp ytfgqgt kleikrrvkfsrsadapayqqgqnqlynelnlgrreeydvldkrrgrdpemggkpqrrknpqeglynelqk dkmaeays eigmkgerrrgkghdglyqglstatkdtydalhmqalppr |
| GPC3-28z | 22 | evqlvqsgaevkkpgasvkvsckasgytfsdyemhwvrqapgqglewmgaihpgsgdta ynqrfkgrvtitadkststaymelsslrsedtavyycarfysyaywgqgtlvtvsagggg sggggsggggsdivmtqtplslpvtpgepasiscrssqslvhsngntylqwylqkpgqspql liykvsnrfsgvpdrfsgsgsgtdftlkisrveaedvgvyycsqsiyvpytfgqgtkleikrt ttpaprpptpaptiasqplslrpeacrpaaggavhtrgldfacdfwvlvvvggvlacysllv tvafiifwvrskrsrllhsdymnmtprrpgptrkhyqpyapprdfaayrsrvkfsrsadapa |

| Names | SEQ ID NO: | Sequences |
|---|---|---|
| | | yqqgqnqlynelnlgrreeydvldkrrgrdpemggkpqrrknpqeglynelqkdkmaea yseigmkgerrrgkghdglyqglstatkdtydalhmqalppr |
| GPC3-BBZ | 23 | evqlvqsgaevkkpgasvkvsckasgytfsdyemhwvrqapgqglewmgaihpgsgdta ynqrfkgrvtitadkststaymelsslrsedtavyycarfysyaywgqgtlvtvsagggg sggggsggggsdivmtqtplslpvtpgepasiscrssqslvhsngntylqwylqkpgqspql liykvsnrfsgvpdrfsgsgsgtdftlkisrveaedvgvyycsqsiyvpytfgqgtkleikrt ttpaprpptpaptiasqplslrpeacrpaaggavhtrgldfacdiyiwaplagtcgvlllslv itlyckrgrkkllyifkqpfmrpvqttqeedgcscrfpeeeeggcelrvkfsrsadapaykq gqnqlynelnlgrreeydvldkrrgrdpemggkprrknpqeglynelqkdkmaeaysei gmkgerrrgkghdglyqglstatkdtydalhmqalppr |
| GPC3-28BBZ | 24 | evqlvqsgaevkkpgasvkvsckasgytfsdyemhwvrqapgqglewmgaihpgsgdta ynqrfkgrvtitadkststaymelsslrsedtavyycarfysyaywgqgtlvtvsagggg sggggsggggsdivmtqtplslpvtpgepasiscrssqslvhsngntylqwylqkpgqspql liykvsnrfsgvpdrfsgsgsgtdftlkisrveaedvgvyycsqsiyvpytfgqgtkleikrt ttpaprpptpaptiasqplslrpeacrpaaggavhtrgldfacdfwvlvvvggvlacysll vtvafiifwvrskrsrllhsdymnmtprrpgptrkhyqpyapprdfaayrskrgrkkllyi fkqpfmrpvqttqeedgcscrfpeeeeggcelrvkfsrsadapayqqgqnqlynelnlgr reeydvldkrrgrdpemggkpqrrknpqeglynelqkdkmaeayseigmkgerrrgkg hdglyqglstatkdtydalhmqalppr |

All documents mentioned in the present invention are cited as references in this application, as if each document is individually cited as a reference. In addition, it should be understood that after reading the above teaching content of the present invention, those skilled in the art may make various changes or modifications to the present invention, and these equivalent forms also fall within the scope defined by the appended claims of the present application.

The invention claimed is:

1. A method for treating a tumor or for reducing the growth, survival or viability of cancer cells, characterized in that an immune effector cell and a second therapeutic agent are administered to a human suffering from a tumor, wherein the immune effector cell expresses a receptor recognizing glypican-3 (GPC3) and the second therapeutic agent comprises a compound of formula II:

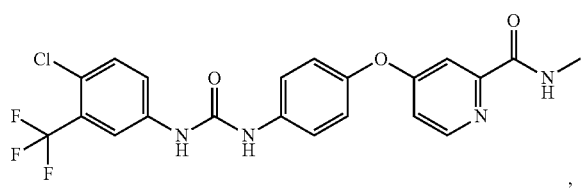

II wherein the immune effector cell is a T cell,
wherein the receptor comprises a chimeric antigen receptor (CAR),
wherein the chimeric antigen receptor comprises an antibody or a fragment thereof that specifically recognizes a tumor antigen, the transmembrane region of CD28, the co-stimulatory signal domain of CD28, and the intracellular domain of CD3ζ,
wherein the antibody specifically recognizing a tumor antigen comprises HCDR1, HCDR2, HCDR3 respectively represented by SEQ ID NOs: 15, 16, 17, and LCDR1, LCDR2, LCDR3 respectively represented by SEQ ID NOs: 18, 19, 20.

2. The method according to claim 1, characterized in that the human is not subjected or is subjected to lymphocyte clearance before administering the immune effector cell to the human suffering from a tumor.

3. The method according to claim 1, characterized in that the second therapeutic agent is administered at a dose of 100-1000 mg per day.

4. The method according to claim 3, characterized in that the dose of the immune effector cell per administration is about $1 \times 10^5$-$1 \times 10^8$ cells/kg subject weight.

5. The method according to claim 1, characterized in that the immune effector cell and the second therapeutic agent are administered in no particular order.

6. The method according to claim 1, characterized in that the tumor comprises: breast cancer, glioma, blood cancer, colon cancer, rectal cancer, renal cell carcinoma, liver cancer, lung cancer, small intestine cancer, esophageal cancer, melanoma, bone cancer, pancreatic cancer, skin cancer, head and neck cancer, skin or intraocular malignant melanoma, uterine cancer, ovarian cancer, rectal cancer, anal cancer, stomach cancer, testicular cancer, uterine cancer, fallopian tube cancer, endometrial cancer, cervical cancer, vagina cancer, vulva cancer, Hodgkin's disease, non-Hodgkin's lymphoma, endocrine system cancer, thyroid cancer, parathyroid cancer, adrenal cancer, soft tissue sarcoma, urethral cancer, penile cancer, childhood solid tumor, bladder cancer, renal or ureteral cancer, renal pelvis cancer, central nervous system (CNS) tumor, primary CNS lymphoma, tumor angiogenesis, spinal tumor, brainstem glioma, pituitary adenoma, Kaposi's sarcoma, epidermoid carcinoma, squamous cell carcinoma, T-cell lymphoma, environmentally induced cancer, a combination of the cancers, and the metastatic foci of the cancer.

7. A kit for treating a tumor, characterized in that the kit comprises:
1) an immune effector cell expressing a receptor that recognizes glypican-3 (GPC3),
wherein the immune effector cell is a T cell,
wherein the receptor comprises a chimeric antigen receptor (CAR),
wherein the chimeric antigen receptor comprises an antibody or a fragment thereof that specifically recognizes a tumor antigen, the transmembrane region of CD28, the co-stimulatory signal domain of CD28, and the intracellular domain of CD3ζ, wherein the antibody specifically recognizing a tumor antigen comprises HCDR1, HCDR2, HCDR3 respectively represented by SEQ ID NOs: 15, 16, 17, and LCDR1, LCDR2, LCDR3 respectively represented by SEQ ID NOs: 18, 19, 20;

2) a second therapeutic agent;

3) a container for containing the above substances of 1) and 2); and 4) instructions for using the kit to treat a tumor in a human;

wherein the immune effector cell and the second therapeutic agent comprises a compound of formula II:

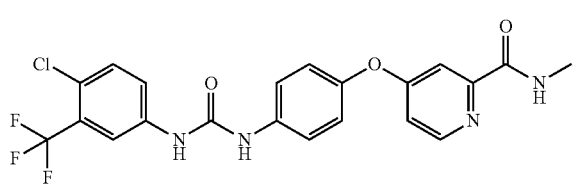

II

8. The method according to claim 1, wherein the second therapeutic agent is administered at a dose of 400-800 mg per day.

9. The method according to claim 1, wherein the second therapeutic agent is administered 1-3 times per day.

10. The method according to claim 1, characterized in that the immune effector cell is administered during the administration of the second therapeutic agent or the second therapeutic agent is administered orally.

11. The method according to claim 1, characterized in that the amino acid sequence of the antibody specifically recognizing the tumor antigen has at least 90% identity with the sequence of SEQ ID NO: 14.

12. The method according to claim 1, characterized in that the amino acid sequence of the chimeric antigen receptor having the antibody that specifically recognizes the tumor antigen has at least 90% identity with the sequence of SEQ ID NO: 22.

13. The method according to claim 2, characterized in that the lymphatic clearance comprises administering one or more chemotherapeutic agents including cyclophosphamide and/or fludarabine.

14. The method according to claim 1, characterized in that the immune effector cell is administered about $5\times10^8$ cells/subject every time for 2 consecutive days.

15. The method according to claim 1, characterized in that the immune effector cell is administered twice.

16. The method according to claim 3, characterized in that the dose of the immune effector cell per administration is about $1\times10^5$-$1\times10^7$ cells/kg subject weight.

* * * * *